(12) United States Patent
Brady et al.

(10) Patent No.: US 6,174,858 B1
(45) Date of Patent: Jan. 16, 2001

(54) CONJUGATES USEFUL IN THE TREATMENT OF PROSTATE CANCER

(75) Inventors: Stephen F. Brady, Philadelphia; Dong-Mei Feng; Victor M. Garsky, both of Blue Bell, all of PA (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/193,365

(22) Filed: Nov. 17, 1998

Related U.S. Application Data

(60) Provisional application No. 60/067,110, filed on Dec. 2, 1997, now abandoned.

(51) Int. Cl.[7] .......................... A61K 38/00; C07K 17/00; C07K 17/06
(52) U.S. Cl. .................... 514/12; 530/362; 530/363; 530/391; 530/405; 530/409; 530/828; 514/21; 424/178.1; 424/193.1; 424/194.1
(58) Field of Search ................................ 530/363, 362, 530/391, 405, 409, 828; 514/12.21; 424/178.1, 193.1, 194.1

(56) References Cited

U.S. PATENT DOCUMENTS

| | | | |
|---|---|---|---|
| 4,203,898 | 5/1980 | Cullinan et al. | 424/262 |
| 4,296,105 | 10/1981 | Baurain et al. | 424/180 |
| 4,376,765 | 3/1983 | Trouet et al. | 424/177 |
| 4,639,456 | 1/1987 | Trouet et al. | 514/18 |
| 4,703,107 | 10/1987 | Monsigny et al. | 530/330 |
| 4,719,312 | 1/1988 | Firestone | 564/510 |
| 4,870,162 | * 9/1989 | Tronet et al. | 530/363 |
| 5,024,835 | 6/1991 | Rao et al. | 530/324 |
| 5,391,723 | 2/1995 | Priest | 536/23.1 |
| 5,599,686 | 2/1997 | DeFeo-Jones et al. | 435/18 |
| 5,621,002 | 4/1997 | Bosslet et al. | 514/451 |
| 5,866,679 | * 2/1999 | De Feo-Jones et al. | 530/322 |
| 5,948,750 | * 9/1999 | Garsky et al. | 514/2 |
| 5,962,216 | * 10/1999 | Trouet et al. | 435/4 |
| 5,998,362 | * 12/1999 | Feng et al. | 514/12 |

FOREIGN PATENT DOCUMENTS

| | | |
|---|---|---|
| B-32486/95 | 8/1995 | (AU) . |
| 0 126 344 A2 | 5/1984 | (EP) . |
| WO 96/00503 | 1/1996 | (WO) . |
| WO 98/13059 | 9/1996 | (WO) . |
| WO 97/12624 | 4/1997 | (WO) . |
| WO 97/14416 | 4/1997 | (WO) . |
| WO 98/10651 | 3/1998 | (WO) . |
| WO 98/40738 | 3/1998 | (WO) . |
| WO 98/18493 | 5/1998 | (WO) . |
| WO 98/52966 | 5/1998 | (WO) . |

OTHER PUBLICATIONS

J. Med. Chem., vol. 28, pp. 1079–1088 (1985), by Rao, et al.
J. Med. Chem., vol. 23, pp. 1166–1170 (1980), by Masquelier, et al.
J. Med. Chem., vol. 23, pp. 1171–1174 (1980), by Baurain, et al.
Science, vol. 261, pp. 212–215 (1993), by Trail, et al.

* cited by examiner

Primary Examiner—F. T. Moezie
(74) Attorney, Agent, or Firm—Dianne Pecoraro; Mark R. Daniel

(57) ABSTRACT

Chemical conjugates which comprise oligopeptides, having amino acid sequences that are selectively proteolytically cleaved by free prostate specific antigen (PSA) and known cytotoxic agents are disclosed. The conjugates of the invention are characterized by attachment of the cleavable oligopeptide to the oxygen atom at the 4-position on a vinca drug that has be desacetylated. Such conjugates are useful in the treatment of prostatic cancer and benign prostatic hypertrophy (BPH).

14 Claims, No Drawings

CONJUGATES USEFUL IN THE TREATMENT OF PROSTATE CANCER

DOMESTIC PRIORITY CLAIM

This application claims priority from the U.S. Provisional application Ser. No. 60/067,110, filed on Dec. 2, 1997, now abandoned.

BACKGROUND OF THE INVENTION

In 1996 cancer of the prostate gland was expected to be diagnosed in 317,000 men in the U.S. and 42,000 American males die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1 - antichymotrypsin is the predominant molecular form of serum PSA and may account for up to 95% of the detected serum PSA (Christensson, A., Bjork, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1 - antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2 - macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Björk, T., Nilsson, O., et al. (1993). J. Urol.. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since there is considerable (100 to 1000 fold) molar excess of both unreacted alpha 1 - antichymotrypsin and alpha 2 - macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M.S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in prostatectomized patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

It is the object of this invention to provide a novel anti-cancer composition useful for the treatment of prostate cancer which comprises oligopeptides, that are selectively proteolytically cleaved by free prostate specific antigen (PSA), in conjugation with a vinca alkaloid cytotoxic agent.

Another object of this invention is to provide a method of treating prostate cancer which comprises administration of the novel anti-cancer composition.

SUMMARY OF THE INVENTION

Chemical conjugates which comprise oligopeptides, having amino acid sequences that are selectively proteolytically cleaved by free prostate specific antigen (PSA), and a vinca alkaloid cytotoxic agent are disclosed. The conjugates of the invention are characterized by attachment of the cleavable oligopeptide to the oxygen atom at the 4-position on a vinca drug that has been desacetylated. Such conjugates are useful in the treatment of prostatic cancer and benign prostatic hyperplasia (BPH).

DETAILED DESCRIPTION OF THE INVENTION

The instant invention relates to novel anti-cancer compositions useful for the treatment of prostate cancer. Such compositions comprise an oligopeptide covalently bonded, optionally through a chemical linker, to a vinca alkaloid cytotoxic agent. The point of attachment of the oligopeptide to the vinca alkaloid cytotoxic agent is at the oxygen atom in the 4-position of the vinca alkaloid cytotoxic agent. It is understood that those vinca alkaloid cytotoxic agents having an acetyl moiety on the oxygen atom in the 4-position must first be desacetylated prior to the formation of the instant conjugates. The oligopeptides are chosen from oligomers that are selectively recognized by the free prostate specific antigen (PSA) and are capable of being proteolytically cleaved by the enzymatic activity of the free prostate specific antigen. Such a combination of an oligopeptide and cytotoxic agent may be termed a conjugate.

Ideally, the cytotoxic activity of the vinca drug is greatly reduced or absent when the oligopeptide containing the PSA proteolytic cleavage site is attached, either directly or through a chemical linker, to the vinca drug and is intact. Also ideally, the cytotoxic activity of the vinca drug increases significantly or returns to the activity of the unmodified vinca drug upon proteolytic cleavage of the attached oligopeptide at the peptide bond where the oplipogopeptide is cleaved by free PSA and any subsequent hydrolysis by endogenous amino peptidases.

Furthermore, it is preferred that the oligopeptide is selected from oligopeptides that are not cleaved or are cleaved at a much slower rate in the presence of non-PSA proteolytic enzymes, such as those enzymes endogenous to human serum, prior to cleavage by free PSA when compared to the cleavage of the oligopeptides in the presence of free enzymatically active PSA. It has been discovered that preferably the amino acid at the point of attachment of the oligopeptide to the vinca drug or the optional linker is a secondary amino acid, selected from the group comprising proline, 3-hydroxyproline, 3-fluoroproline, pipecolic acid, 3-hydroxypipecolic acid, 2-azetidine, 3-hydroxy-2-azetidine, sarcosine and the like. More preferably, the amino acid at the point of attachment of the oligopeptide to the vinca drug or the optional linker is a cyclic amino acid, selected from the group comprising proline, 3-hydroxyproline, 3-fluoroproline, pipecolic acid, 3-hydroxypipecolic acid, 2-azetidine, 3-hydroxy-2-azetidine and the like.

For the reasons above, it is desireable for the oligopeptide to comprise a short peptide sequence, preferably less than ten amino acids. Most preferably the oligopeptide comprises seven or six amino acids. Because the conjugate preferably comprises a short amino acid sequence, the solubility of the conjugate may be influenced to a greater extent by the generally hydrophobic character of the cytotoxic agent component. Therefore, amino acids with hydrophilic substituents may be incorporated in the oligopeptide sequence or N-terminus blocking groups may be selected to offset or diminish such a hydrophobic contribution by the cytotoxic agent.

While it is not necessary for practicing this aspect of the invention, a preferred embodiment of this invention is a conjugate wherein the oligopeptide, and the optional chemical linker if present are detached from the cytotoxic agent by the proteolytic activity of the free PSA and any other native proteolytic enzymes present in the tissue proximity, thereby presenting the cytotoxic agent, or a cytotoxic agent that retains part of the oligopeptide/linker unit but remains cytotoxic, into the physiological environment at the place of proteolytic cleavage. Pharmaceutically acceptable salts of the conjugates are also included.

It is understood that the oligopeptide that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage. The term "selective" as used in connection with the proteolytic PSA cleavage means a greater rate of cleavage of an oligopeptide component of the instant invention by free PSA relative to cleavage of an oligopeptide which comprises a random sequence of amino acids. Therefore, the oligopeptide component of the instant invention is a prefered substrate of free PSA. The term "selective" also indicates that the oligopeptide is proteolytically cleaved by free PSA between two specific amino acids in the oligopeptide.

The oligopeptide components of the instant invention are selectively recognized by the free prostate specific antigen (PSA) and are capable of being proteolytically cleaved by the enzymatic activity of the free prostate specific antigen. Such oligopeptides comprise an oligomer selected from:
 a) AsnLysIleSerTyrGlnIlSer (SEQ.ID.NO.: 1),
 b) LysIleSerTyrGlnIlSer (SEQ.ID.NO.: 2),
 c) AsnLysIleSerTyrTyrlSer (SEQ.ID.NO.: 3),
 d) AsnLysAlaSerTyrGlnIlSer (SEQ.ID.NO.: 4),
 e) SerTyrGlnIlSerSer (SEQ.ID.NO.: 5);
 f) LysTyrGlnIlSerSer (SEQ.ID.NO.: 6);
 g) hArgTyrGlnIlSerSer (SEQ.ID.NO.: 7);
 h) hArgChaGlnIlSerSer (SEQ.ID.NO.: 8);
 i) TyrGinlSerSer (SEQ.ID.NO.: 9);
 j) TyrGlnIlSerLeu (SEQ.ID.NO.: 10);
 k) TyrGlnIlSerNle (SEQ.ID.NO.: 11);
 l) ChgGlnIlSerLeu (SEQ.ID.NO.: 12);
 m) ChgGlnIlSerNle (SEQ.ID.NO.: 13);
 n) SerTyrGInlSer (SEQ.ID.NO.: 14);
 o) SerChgGlnIlSer (SEQ.ID.NO.: 15);
 p) SerTyrGlnIlSerVal (SEQ.ID.NO.: 16);
 q) SerChgGlnIlSerVal (SEQ.ID.NO.: 17);
 r) SerTyrGlnIlSerLeu (SEQ.ID.NO.: 18);
 s) SerChgGlnIlSerLeu (SEQ.ID.NO.: 19);
 t) HaaXaaSerTyrGlnSer (SEQ.ID.NO.: 20);
 u) HaaXaaLysTyrGlnIlSer (SEQ.ID.NO.: 21);
 v) HaaXaahArgTyrGlnIlSer (SEQ.ID.NO.: 22);
 w) HaaXaahArgChaGlnIlSer (SEQ.ID.NO.: 23);
 x) HaaTyrGlnIlSer (SEQ.ID.NO.: 24);
 y) HaaXaaSerChgGlnIlSer (SEQ.ID.NO.: 25);
 z) HaaChgGlnIlSer (SEQ.ID.NO.: 26);
wherein Haa is a cyclic amino acid substituted with a hydrophilic moiety, hArg is homoarginine, Xaa is any amino acid, Cha is cyclohexylalanine and Chg is cyclohexylglycine.

In an embodiment of the instant invention, the oligopeptide comprises an oligomer that is selected from:
 a) SerSerTyrGlnIlSerAla (SEQ.ID.NO.: 27);
 b) SerSerChgGlnIlSerSer (SEQ.ID.NO.: 28);
 c) SerSerTyrGlnIlSerAla (SEQ.ID.NO.: 29);
 d) SerSerChgGlnIlSerSer (SEQ.ID.NO.: 30);
 e) 4-HypSerSerTyrGlnIlSer (SEQ.ID.NO.: 31);
 f) 4-HypSerSerChgGlnIlSer (SEQ.ID.NO.: 32);
 h) AlaSerTyrGlnIlSerSer (SEQ.ID.NO.: 33);

i) AlaSerChgGlnIServer (SEQ.ID.NO.: 34);
j) AlaSerTyrGlnlSerAla (SEQ.ID.NO.: 35);
k) AlaSerChgGlnlSerAla (SEQ.ID.NO.: 36);
l) 4-HypAlaSerTyrGlnlSer (SEQ.ID.NO.: 37);
m) 4-HypAlaSerChgGlnlSer (SEQ.ID.NO.: 38);
wherein 4-Hyp is 4-hydroxyproline, Xaa is any amino acid, hArg is homoarginine, Cha is cyclohexylalanine and Chg is cyclohexylglycine.

In a more preferred embodiment of the instant invention, the oligopeptide comprises an oligomer selected from:
SerSerChgGlnlSerAlaPro (SEQ.ID.NO.: 39);
SerSerChgGlnlSerSerPro (SEQ.ID.NO.: 40);
SerSerChgGlnlSerAla4-Hyp (SEQ.ID.NO.: 41);
SerSerChgGlnlSerSer4-Hyp (SEQ.ID.NO.: 42);
AbuSerSerChgGlnlSerPro (SEQ.ID.NO.: 43);
AbuSerSerChgGlnlSer4-Hyp (SEQ.ID.NO.: 44);
SerSerSerChgGlnlSerLeuPro (SEQ.ID.NO.: 45);
SerSerSerChgGlnlSerValPro (SEQ.ID.NO.: 46);
SerAlaSerChgGlnlSerLeu4-Hyp (SEQ.ID.NO.: 47);
SerAlaSerChgGlnlSerValPro (SEQ.ID.NO.: 48);
(N-methyl-Ser)SerSerChgGlnlSerLeuPip (SEQ.ID.NO.: 49);
(N-methyl-Ser)SerSerChgGlnlSerValPip (SEQ.ID.NO.: 50);
4-HypSerSerTyrGlnISerSerPro (SEQ.ID. NO.: 5 1);
4-HypSerSerTyrGlnlSerSer4-Hyp (SEQ.ID.NO.: 52);
4-HypSerSerTyrGIniSerSerPro (SEQ.ID.NO.: 53);
4-HypS erS erTyrGinISerSerSer (SEQ.ID.NO.: 54);
4-HypSerSerTyrGlnlSer4-Hyp (SEQ.ID.NO.: 55);
4-HypSerSerChgGlnlSerPro (SEQ.ID.NO.: 56);
4-HypSerSerChgGlnlSerSerPro (SEQ.ID.NO.: 57);
4-HypSerSerChgGlnlSerLeu (SEQ.ID.NO.: 58);
4-HypSerSerChgGlnlSerVal (SEQ.ID.NO.: 59);
4-HypAlaSerChgGlnlSerValPro (SEQ.ID.NO.: 60);
4-HypAlaSerChgGlnlSerSerPip (SEQ.ID.NO.: 61);
4-HypSerSerChgGlnlSer (SEQ.ID.NO.: 62);
4-HypSerSerChgGlnISerGly (SEQ.ID.NO.: 63);
SerSerChgGlnlSerGly (SEQ.ID.NO.: 64);
3-PalSerSerTyrGlnISer4-Hyp (SEQ.ID.NO.: 65);
3-PalSerSerChgGlnlSerPro (SEQ.ID.NO.: 66);
(3,4-DiHyp)SerSerTyrGlnlSerSerPro (SEQ.ID.NO.: 67); and
(3,4-DiHyp)SerSerTyrGlnlSerSer4-Hyp (SEQ.ID.NO.: 68);
wherein Abu is aminobutyric acid, 4-Hyp is 4-hydroxyproline, Pip is pipecolic acid, 3,4-DiHyp is 3,4-dihydroxyproline, 3-Pal is 3-pyridylalanine, Sar is sarcosine and Chg is cyclohexylglycine.

The phrase "oligomers that comprise an amino acid sequence" as used hereinabove, and elsewhere in the Detailed Description of the Invention, describes oligomers of from about 3 to about 100 amino acids residues which include in their amino acid sequence the specific amino acid sequence decribed and which are therefore proteolytically cleaved within the amino acid sequence described by free PSA. Preferably, the oligomer is from 5 to 10 amino acid residues. Thus, for example, the following oligomer: hArg-SerAlaChgGlnlSerLeu (SEQ.ID.NO.: 69); comprises the amino acid sequence: ChgGlnlSerLeu (SEQ.ID.NO.: 12); and would therefore come within the instant invention. And the oligomer: hArgSer4-HypChgGlnlSerLeu (SEQ.ID.NO.: 70); comprises the amino acid sequence: 4-HypChgGlnlSerLeu (SEQ.ID.NO.: 71); and would therefore come within the instant invention. It is understood that such oligomers do not include semenogelin I and semenogelin II.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. Certain unnatural and modified natural amino acids may also be utilized to replace the corresponding natural amino acid in the oligopeptides of the instant invention. Thus, for example, tyrosine may be replaced by 3-iodotyrosine, 2-methyltyrosine, 3-fluorotyrosine, 3-methyltyrosine and the like. Further for example, lysine may be replaced with N'-(2-imidazolyl)lysine and the like. The following list of amino acid replacements is meant to be illustrative and is not limiting:

| Original Amino Acid | Replacement Amino Acid(s) |
| --- | --- |
| Ala | Gly, Abu |
| Arg | Lys, Ornithine |
| Asn | Gln |
| Asp | Glu |
| Glu | Asp |
| Gln | Asn |
| Gly | Ala |
| Ile | Val, Leu, Met, Nle, Nva |
| Leu | Ile, Val, Met, Nle, Nva |
| Lys | Arg, Ornithine |
| Met | Leu, Ile, Nle, Val |
| Ornithine | Lys, Arg |
| Phe | Tyr, Trp |
| Ser | Thr, Abu, Hyp, Ala |
| Thr | Ser, Abu, Hyp |
| Trp | Phe, Tyr |
| Tyr | Phe, Trp |
| Val | Leu, Ile, Met, Nle, Nva |

Thus, for example, the following oligopeptides may be synthesized by techniques well known to persons of ordinary skill in the art and would be expected to be proteolytically cleaved by free PSA:
AsnArgIleSerTyrGlnlSer (SEQ.ID.NO.: 72)
AsnLysValSerTyrGlnlSer (SEQ.ID.NO.: 73)
AsnLysMetSerTyrGlnlSerSer (SEQ.ID.NO.: 74)
AsnLysLeuSerTyrGlnlSerSer (SEQ.ID.NO.: 75)
AsnLyslIeSerTyrGlnISer (SEQ.ID.NO.: 76)
GlnLysIIeSerTyrGlnlSerSer (SEQ.ID.NO.: 77).
Asn4-HypIIeSerTyrGlnlSer (SEQ.ID.NO.: 78)
Asn4-HypValSerTyrGlnlSer (SEQ.ID.NO.: 79)
4-HypAlaSerTyrGlnlSerSer (SEQ.ID.NO.: 80)
(3,4-dihydroxyproline)AlaSerTyrGlnlSerSer (SEQ.ID.NO.: 81)
3-hydroxyprolineSerChgGnISer (SEQ.ID.NO.: 82)
4-HypAlaSerChgGlnlSerSer (SEQ.ID.NO.: 83).

The compounds of the present invention may have asymmetric centers and occur as racemates, racernic mixtures, and as individual diastereomers, with all possible isomers, including optical isomers, being included in the present invention. Unless otherwise specified, named amino acids are understood to have the natural "L" stereoconfiguration In the present invention, the amino acids which are disclosed are identified both by conventional 3 letter and single letter abbreviations as indicated below:

| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The following abbreviations are utilized in the specification and figures to denote the indicated amino acids and moieties:

hR or hArg: homoarginine
hY or hTyr: homotyrosine
Cha: cyclohexylalanine
Amff: 4-aminomethylphenylalanine
DAP: 1,3-diaminopropyl
DPL: 2-(4,6-dimethylpyrimidinyl)lysine
(imidazolyl)K: N'-(2-imidazolyl)lysine
$Me_2PO_3$-Y: O-dimethylphosphotyrosine
O—Me—Y: 0-methyltyrosine
TIC: 1,2,3,4-tetrahydro-3-isoquinoline carboxylic acid
DAP: 1,3-diaminopropane
TFA: trifluoroacetic acid
AA: acetic acid
3PAL: 3-pyridylalanine
4-Hyp: 4-hydroxyproline
dAc-Vin: 4-des- acetylvinblastine
Pip: pipecolic acid
Abu: 2-aminobutyric acid
Nva: norvaline It is well known in the art, and understood in the instant invention, that peptidyl therapeutic agents such as the instant oligopeptide-cytotoxic agent conjugates preferably have the terminal amino moiety of any oligopeptide substituent protected with a suitable protecting group, such as acetyl, benzoyl, pivaloyl and the like. Such protection of the terminal amino group reduces or eliminates the enzymatic degradation of such peptidyl therapeutic agents by the action of exogenous amino peptidases which are present in the blood plasma of warm blooded animals. Such protecting groups also include hydrophilic blocking groups, which are chosen based upon the presence of hydrophilic functionality. Blocking groups that increase the hydrophilicity of the conjugates and therefore increase the aqueous solubility of the conjugates include but are not limited to hydroylated alkanoyl, polyhydroxylated alkanoyl, polyethylene glycol, glycosylates, sugars and crown ethers. N-Terminus unnatural amino acid moieties may also ameleorate such enzymatic degradation by exogenous amino peptidases.

Preferably the N-terminus protecting group is selected from a) acetyl;

b) 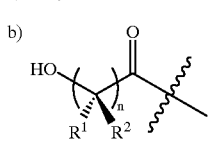

c) 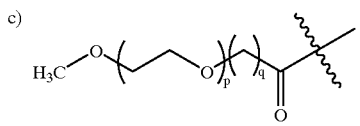

d) 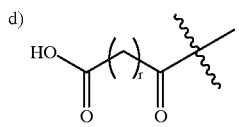

wherein:

$R^1$ and $R^2$ are independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^3O$—, $R^3C(O)NR^3$—, $(R^3)_2NC(O)$—, $R^3_2N$—C$(NR^3)$—, $R^4S(O)_2NH$, CN, $NO_2$, $R^3C(O)$—, $N_3$, —$N(R^3)_2$, or $R^4OC(O)NR^3$—, c) unsubstituted $C_1$-$C_6$ alkyl, d) substituted $C_1$-$C_6$ alkyl wherein the substituent on the substituted $C_1$-$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^3O$—, $R^4S(O)_2NH$, $R^3C(O)NR^3$—, $(R^3)_2NC(O)$—, $R^3_2N$—C$(NR^3)$—, CN, $R^3C(O)$—, N3, -$N(R^3)$2, and $R^4OC(O)$—$NR^3$—; or $R^1$ and $R^2$ are combined to form —$(CH_2)_s$—wherein one of the carbon atoms is optionally replaced by a moiety selected from: O, S(O)m, —NC(O)—, NH and —N(COR$^4$)—;

$R^3$ is selected from: hydrogen, aryl, substituted aryl, heterocycle, substituted heterocycle, $C_1$–$C_6$ alkyl and $C_3$–$C_{10}$ cycloalkyl;

$R^4$ is selected from: aryl, substituted aryl, heterocycle, substituted heterocycle, $C_1$–$C_6$ alkyl and $C_3$–$C_{10}$ cycloalkyl;

m is 0, 1 or 2;

n is 1, 2, 3 or 4;

p is zero or an integer between 1 and 100; and
q is 0 or 1, provided that if p is zero, q is 1; and
r is 1, 2 or 3;
s is 3, 4 or 5.

Certain of the oligopeptides of the instant conjugates comprise a cyclic amino acid substituted with a hydrophilic moiety, previously represented by the term "Haa", which may also be represented by the formula:

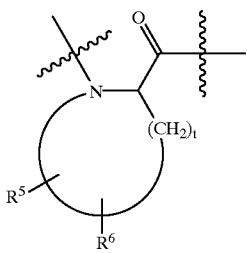

wherein:
$R^5$ is selected from HO— and $C_1$–$C_6$ alkoxy;
$R^6$ is selected from hydrogen, halogen, $C_1$–$C_6$ alkyl, HO— and $C_1$–$C_6$ alkoxy; and
t is 3 or 4.
The structure

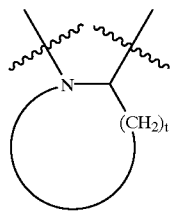

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

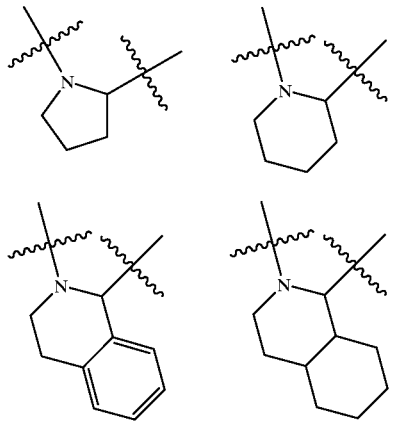

The conjugates of the present invention may have asymmetric centers and occur as racemates, racemic mixtures, and as individual diastereomers, with all possible isomers, including optical isomers, being included in the present invention. When any variable (e.g. aryl, heterocycle, $R^3$ etc.) occurs more than one time in any constituent, its definition on each occurence is independent of every other occurence. For example, $HO(CR^1R^2)_2$— represents $HOCH_2CH_2$—, $HOCH_2CH(OH)$—, $HOCH(CH_3)CH(OH)$-, etc. Also, combinations of substituents and/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aralkyl and aroyl, is intended to mean any stable monocyclic or bicyclic carbon ring of up to 7 members in each ring, wherein at least one ring is aromatic. Examples of such aryl elements include phenyl, naphthyl, tetrahydro-naphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein in the terms "substituted $C_{1-8}$ alkyl", "substituted aryl" and "substituted heterocycle" include moieties containing from 1 to 3 substituents in addition to the point of attachment to the rest of the compound. Such additional substituents are selected from F, Cl, Br, $CF_3$, $NH_2$, N($C_1$–$C_6$ alkyl)$_2$, NO$_2$, CN, ($C_1$–$C_6$ alkyl)O—, —OH, ($C_1$–$C_6$ alkyl)S(O)$_m$—, ($C_1$–$C_6$ alkyl)C(O)NH—, H$_2$N–C(NH)—, ($C_1$–$C_6$ alkyl)C(O)—, ($C_1$–$C_6$ alkyl)OC(O)—, N$_3$, ($C_1$–$C_6$ alkyl)OC(O)NH— and $C_1$–$C_{20}$ alkyl.

When $R^1$ and $R^2$ are combined to form -(CH$_2$)s-, the cyclic moieties and heteroatom-containing cyclic moieties so defined include, but are not limited to:

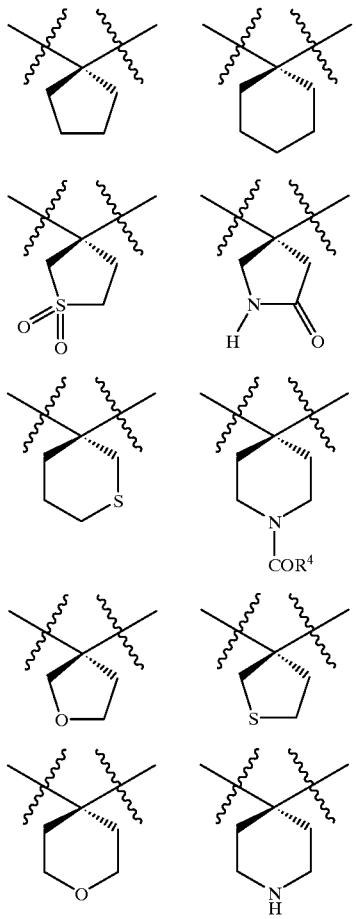

As used herein, the term "hydroxylated" represents substitution on a substitutable carbon of the ring system being so described by a hydroxyl moiety. As used herein, the term "poly-hydroxylated" represents substitution on two or more substitutable carbon of the ring system being so described by 2, 3 or 4 hydroxyl moieties.

As used herein, the term "PEG" represents certain polyethylene glycol containing substituents having the designated number of ethyleneoxy subunits. Thus the term PEG(2) represents

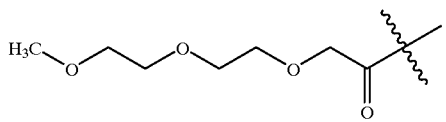

and the term PEG(6) represents

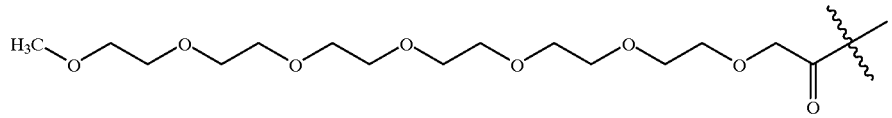

As used herein, the term "(d)(2,3-dihydroxypropionyl)" represents the following structure:

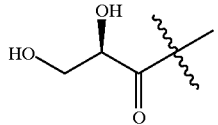

As used herein, the term "(2R,3S) 2,3,4-trihydroxybutanoyl" represents the following structure:

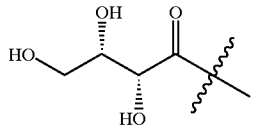

As used herein, the term "quinyl" represents the following structure:

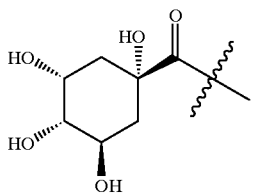

or the diastereomer thereof.

As used herein, the term "cotininyl" represents the following structure:

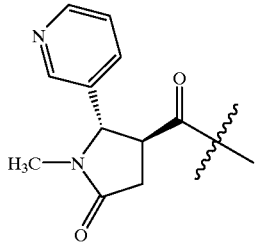

or the diastereomer thereof.

As used herein, the term "gallyl" represents the following structure:

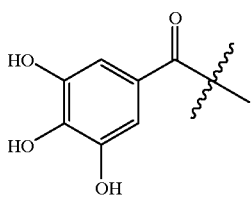

As used herein, the term "4-ethoxysquarate" represents the following structure:

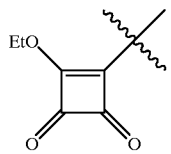

The cytotoxic agent that is utilized in the conjugates of the instant invention may be selected from the vinca alkaloid cytotoxic agents. Particularly useful members of this class include, for example, a vinca alkaloid selected from vinblastine, vincristine, leurosidine, vindesine, vinorelbine, navelbine, leurosine and the like or optical isomers thereof. It is understood that the conjugates of the instant invention have attachment of the oligopeptide through the oxygen atom attached to C-4 of the vinca alkaloid. Therefore, certain of the vinca alkaloids having an acetyl moiety on that oxygen must first be desacetylated before being coupled to the oligopeptide (or the optional linker unit). Furthermore, one skilled in the art may make chemical modifications to the desired cytotoxic agent in order to make reactions of that compound more convenient for purposes of preparing conjugates of the invention.

The preferred group of 4-desacetyl-vinca alkaloid cytotoxic agents for the present invention include drugs of the following formulae:

THE VINCA ALKALOID GROUP OF DRUGS OF FORMULA I:

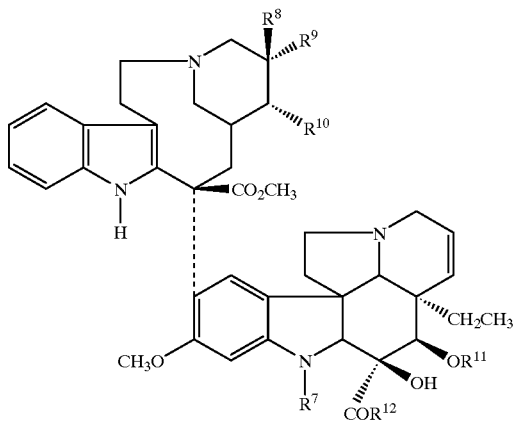

(1)

in which $R^7$ is H, $CH_3$ or CHO;

when $R^9$ and $R^{10}$ are taken singly, $R^{10}$ is H, and one of $R^8$ and $R^9$ is ethyl and the other is H or OH;

when $R^9$ and $R^{10}$ are taken together to form a double bond, $R^8$ is ethyl;

$R^{11}$ is hydrogen;

$R^{12}$ is OH, O—($C_1$–$C_3$ alkyl), or $NH_2$.

The oligopeptide-cytotoxic agent conjugate of the instant invention wherein the cytotoxic agent is the preferred cytotoxic agent 4-O-desacetylvinblastine may be described by the general formula Ia below:

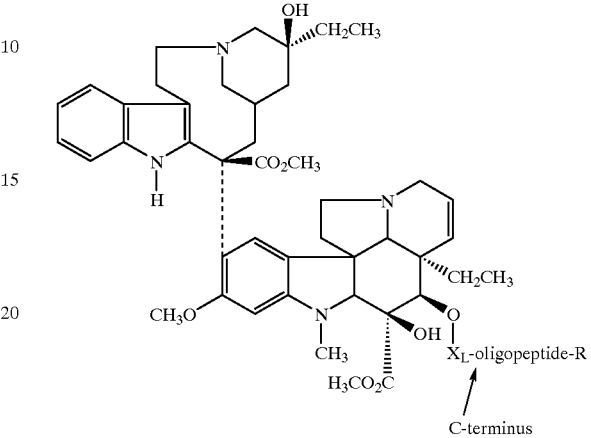

Ia wherein:
oligopeptide is an oligopeptide which is specifically recognized by the free prostate specific antigen (PSA) and is capable of being proteolytically cleaved by the enzymatic activity of the free prostate specific antigen,
$X_L$ is selected from: a bond, —C(O)—($CH_2$)$_u$—W—($CH_2$)$_u$—O— and —C(O)—($CH_2$)$_u$—W—($CH_2$)$_u$—NH—;

R is selected from
a) hydrogen,
b) —(C=O)$R^{1a}$,
c)

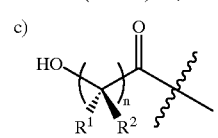

d)

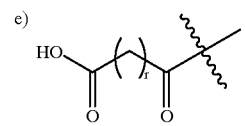

e)

f) ethoxysquarate; and
g) cotininyl;
$R^1$ and $R^2$ are independently selected from: hydrogen, OH, $C_1$–$C_6$ alkyl, $C_1$–$C_6$ alkoxy, $C_1$–$C_6$ aralkyl and aryl;
$R^{1a}$ is $C_1$–$C_6$-alkyl, hydroxylated $C_3$–$C_8$-cycloallyl, polyhydroxylated $C_3$–$C_8$-cycloalkyl, hydroxylated aryl, polyhydroxylated aryl or aryl,
$R^9$ is hydrogen, ($C_1$–$C_3$ alkyl)—CO, or chlorosubstituted ($C_1$–$C_3$ alkyl)—CO;
W is selected from a branched or straight chain $C_1$–$C_6$-alkyl, cyclopentyl, cyclohexyl, cycloheptyl or bicyclo[2.2.2] octanyl;
n is 1, 2, 3 or 4;

p is zero or an integer between 1 and 100;
q is 0 or 1, provided that if p is zero, q is 1;
r is 1, 2 or 3;
t is 3 or 4;
u is 0, 1, 2 or 3,
or the pharmaceutically acceptable salt or optical isomer thereof.

Preferably, $X_L$ is a bond.

In an embodiment of the instant application, the moiety oligopeptide - R is selected from:

Ac-4-trans-L-HypSerSerChgGlnSerSerPro; (SEQ.ID.NO.: 84)
Ac-4-trans-L-HypSerSerChgGlnSerGly; (SEQ.ID.NO.: 85)
Ac-4-trans-L-HypSerSerChgGlnSerSar; (SEQ.ID.NO.: 86)
Ac-4-trans-L-Hyp-Ser-Ser–Chg-Gln-Ser-Ser-Pro; (SEQ.ID.NO.: 87)
Ac-4-trans-L-Hyp-Ser-Ser–Chg-Gln-SerVal; (SEQ.ID.NO.: 88)
Ac-4-trans-L-Hyp-Ser-Ser–Chg-Gln-Ser-Ser-4-trans-L-Hyp; (SEQ.ID.NO.: 89)
Ac-Abu-Ser-Ser–Chg-Gln-Ser-Pro; (SEQ.ID.NO.: 90)
hydroxyacetylAbu-Ser-Ser–Chg-Gln-Ser-Pro; (SEQ.ID.NO.: 91) acetyl3-PALSer-Ser–Chg-Gln-Ser-Ser-Pro; (SEQ.ID.NO.: 92)
Ac--4-trans-L-Hyp-Ser-Ser–Chg-Gln-Ser-Val; (SEQ.ID.NO.: 93)
Ac--4-trans-L-Hyp-Ser-Ser–Chg-Gln-Ser-Leu; (SEQ.ID.NO.: 94)
Ac-4-trans-L-HypSerSerChgGlnSerSer4-trans-L-Hyp; (SEQ.ID.NO.: 95)
Ac-4-trans-L-HypSerSerChgGlnSerPro; (SEQ.ID.NO.: 96)
Ac-SerSerChgGlnSerGly; (SEQ.ID.NO.: 98)
Ac-SerSerChgGlnSerSer-4-trans-L-Hyp; (SEQ.ID.NO.: 99)
Ac-SerSerChgGlnSerSerPro; (SEQ.ID.NO.: 100)
Ac-4-trans-L-HypSerSerChgGlnSerAla; (SEQ.ID.NO.: 103)
Ac-4-trans-L-HypSerSerChgGlnSerChg; (SEQ.ID.NO.: 104)
Ac-4-trans-L-HypSerSerChgGlnSerSar; (SEQ.ID.NO.: 105)
Ac-SerSerChgGinSerSerHyp; (SEQ.ID.NO.: 106)
Ac-4-trans-L-HypSerSerChgGlnSerSerPro; (SEQ.ID.NO.: 107)
Ac-AbuSerSerChgG.nSer(dSer)Pro; (SEQ.ID.NO.: 108)
Ac-AbuSerSerChgGlnSerSerPro; (SEQ.ID.NO.: 109)
Ac-SerSerChgGlnSerSerPro; (SEQ.ID.NO.: 111)
Ac-4-trans-L-HypSerSerChg(dGln)SerSerPro; (SEQ.ID.NO.: 114)
Ac-4-trans-L-HypSerSerChg(dGln)(dSer)SerPro; (SEQ.ID.NO.: 115)
Ac-SerChgGln-SerSerPro; (SEQ.ID.NO.: 116)
Ac-SerChgGlnSerSer-4-trans-L-Hyp; (SEQ.ID.NO.: 117)
Ac--SerChgGlnSerSerSar; (SEQ.ID.NO.: 118)
Ac-SerChgGlnSerSerAibPro; (SEQ.ID.NO.: 119)
Ac-SerChgGlnSerSerN-Me-Ala; (SEQ.ID.NO.: 120)
Ac-4-trans-L-HypSerSerChgGinSerSerPip; (SEQ.ID.NO.: 124) and
Ac-SerChgGlnSerSerN-Me-dA; (SEQ.ID.NO.: 125)
wherein Abu is aminobutyric acid, 4-trans-L-Hyp is 4-trans-L-hydroxyproline, Pip is pipecolinic acid, 3,4-DiHyp is 3,4-dihydroxyproline, 3-PAL is 3-pyridylalanine, Sar is sarcosine and Chg is cyclohexylglycine.

The following compounds are specific examples of the oligopeptide-desacetylvinblastine conjugate of the instant invention:

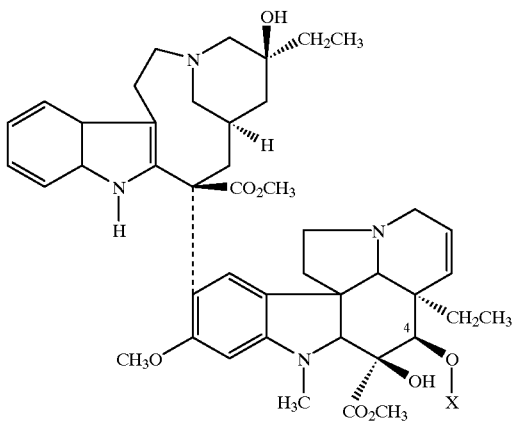

wherein X is

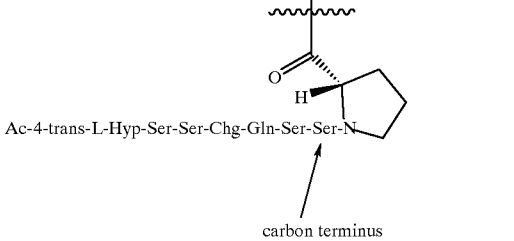

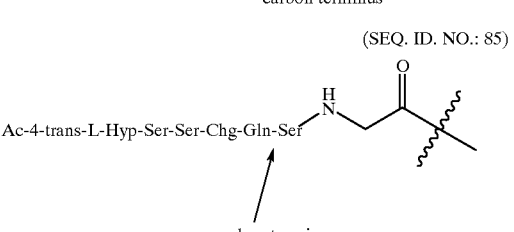

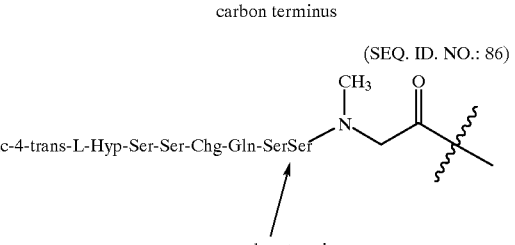

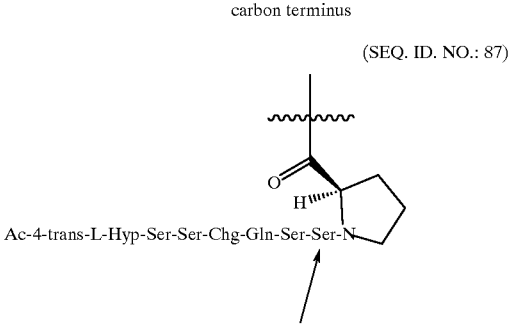

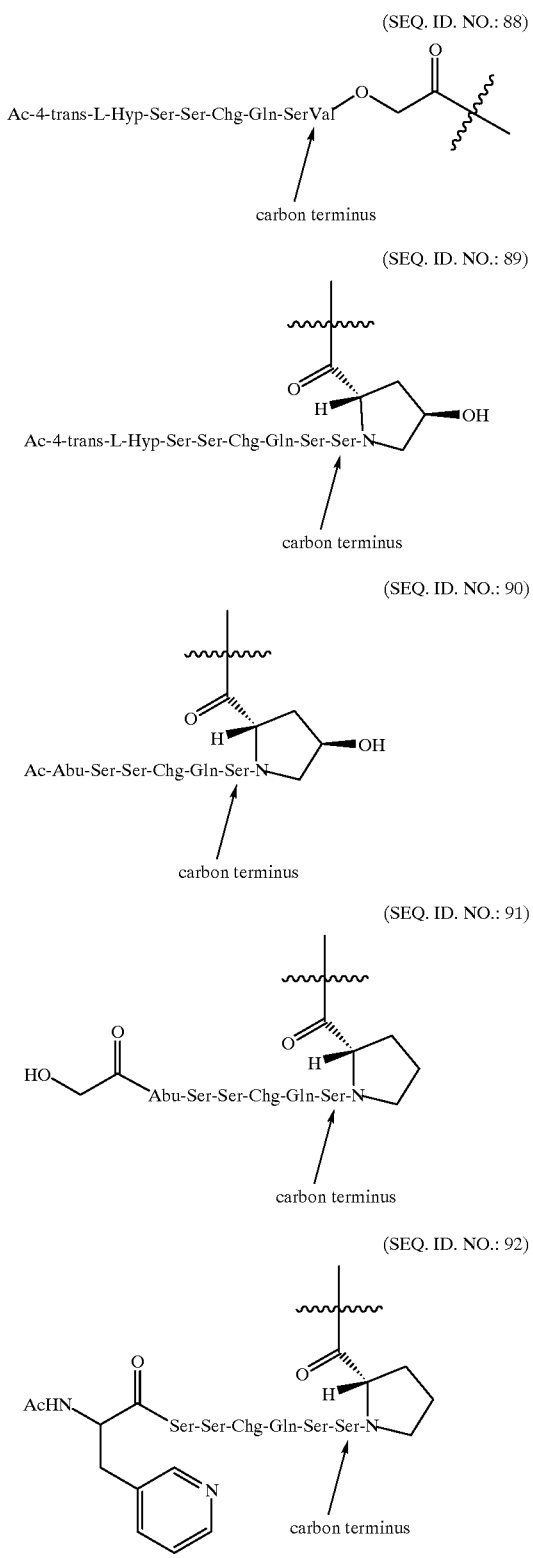

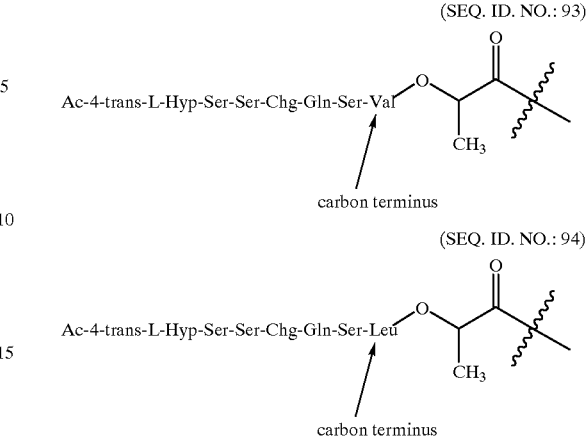

or the pharmaceutically acceptable salt or optical isomer thereof.

The oligopeptides, peptide subunits and peptide derivatives (also termed "peptides") of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1980, and Stewart et al., "Solid Phase Peptide Synthesis", Second Edition, Pierce Chemical Company, 1984. The teachings of these works are hereby incorporated by reference.

The suitably substituted cyclic amino acid having a hydrophilic substituent, which may be incorporated into the instant conjugates by standard peptide synthesis techniques, is itself either commercially available or is readily synthesized by techniques well known in the art or described herein. Thus syntheses of suitably substituted prolines are described in the following articles and references cited therein: J. Ezquerra et al., *J. Org. Chem.* 60: 2925–2930 (1995); P. Gill and W. D. Lubell, *J. Org. Chem.*, 60:2658–2659 (1995); and M. W. Holladay et al., *J. Med. Chem.*, 34:457–461 (1991). The teachings of these works are hereby incorporated by reference.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like.

The conjugates of the instant invention which comprise the oligopeptide containing the PSA cleavage site and a vinca alkaloid cytotoxic agent may be synthesized by techniques well known in the medicinal chemistry art. For example, the hydroxyl moiety on the vinca drug may be covalently attached to the oligopeptide at the carboxyl terminus such that an ester bond is formed. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0]undec-7-ene).

One skilled in the art understands that in the synthesis of compounds of the invention, one may need to protect various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry,* McOmie, ed., Plenum Press, NY, N.Y. (1973); and, *Protective Groups in Organic Synthesis,* Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; Cl–Clo alkanoyloxymethyl such as acetoxymethyl, propionoxymethyl and the like; and groups such as phenacyl, 4-halophenacyl, allyl, dimethylallyl, tri-($C_1$–$C_3$ alkyl) silyl, such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with desacetylvinblastine, the following Reaction Schemes illustrate the synthesis of the conjugates of the instant invention.

Reaction Scheme I illustrates preparation of conjugates of the oligopeptides of the instant invention and the vinca alkaloid cytotoxic agent vinblastine wherein the attachment of the oxygen of the 4-desacetylvinblastine is at the C-terminus of the oligopeptide. While other sequences of reactions may be useful in forming such conjugates, it has been found that initial attachment of a single amino acid to the 4-oxygen and subsequent attachment of the remaining oligopeptide sequence to that amino acid is a preferred method. It has also been found that 3,4-dihydro-3-hydroxy-4-oxo-1,2,3-benzotriazine (ODHBT) may be utilized in place of HOAt in the final coupling step.

Reaction Scheme II illustrates preparation of conjugates of the oligopeptides of the instant invention wherein a hydroxy alkanolyl acid is used as a linker between the vinca drug and the oligopeptide.

REACTION SCHEME I

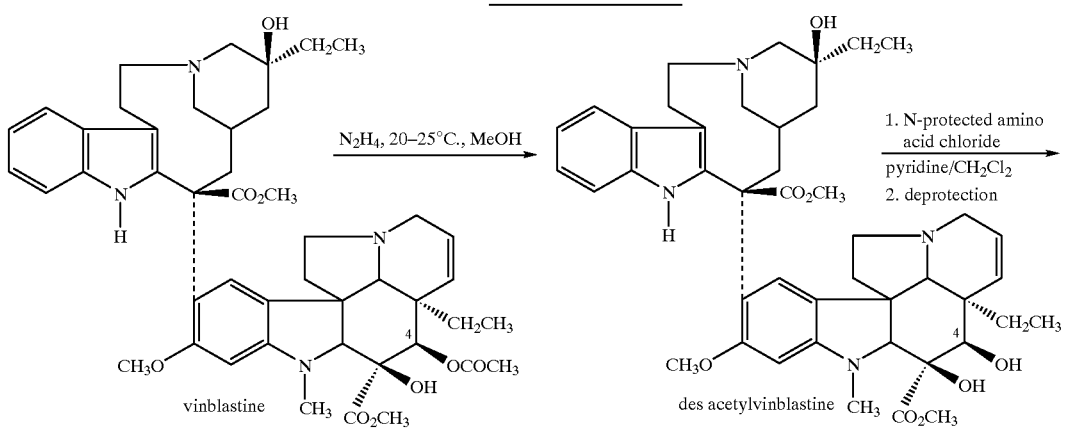

-continued
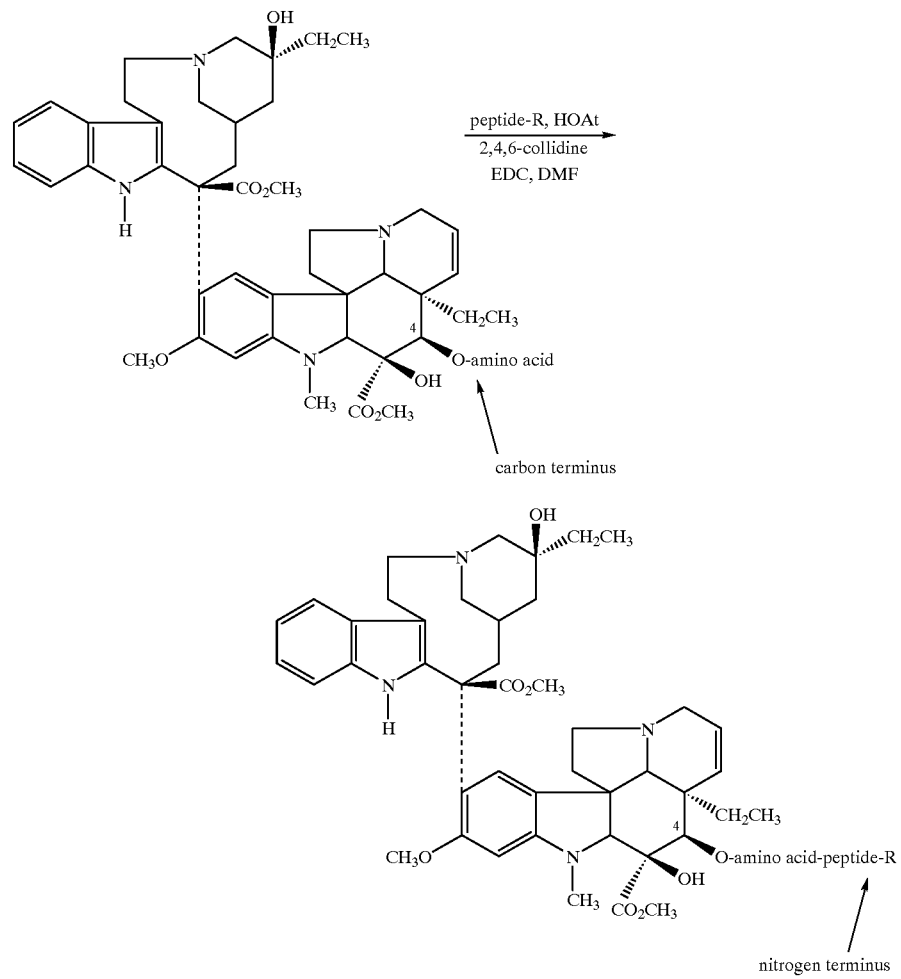
carbon terminus
nitrogen terminus
REACTION SCHEME II
N-protected amino acid
+
HO—(CH$_2$)$_u$W(CH$_2$)$_{u'}$—CO$_2$benzyl
$\xrightarrow{\text{DMAP/DCC}}$
N-protected amino acid-O—(CH$_2$)$_u$W(CH$_2$)$_{u'}$—CO$_2$benzyl
↓ hydrogenation -continued

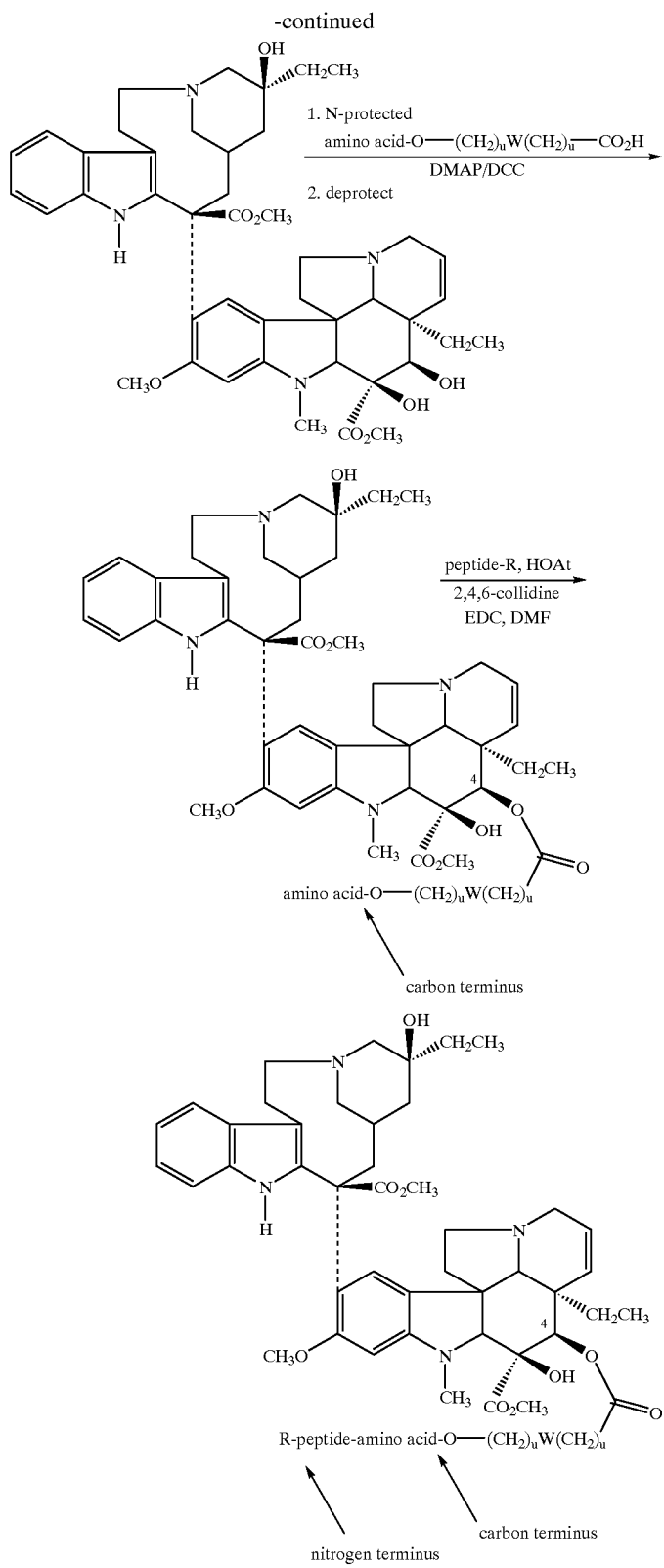

The oligopeptide-cytotoxic agent conjugates of the invention are useful in the treatment of diseases that are characterized by abnormal cells or abnormal proliferation of cells, whether malignant or benign, wherein those cells are characterized by their secretion of enzymatically active PSA. Such diseases include, but are not limited to, prostate cancer, benign prostatic hyperplasia, metastatic prostate cancer, breast cancer and the like.

The oligopeptide-cytotoxic agent conjugates of the invention are administered to the patient in the form of a pharmaceutical composition which comprises a conjugate of of the instant invention and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See e.g. *Remington's Pharmaceutical Sciences*, 16th ed., 1980, Mack Publishing Company, edited by Osol et al Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

As used herein, the term "composition" is intended to encompass a product comprising the specified ingredients in the specific amounts, as well as any product which results, directly or indirectly, from combination of the specific ingredients in the specified amounts.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUSTM model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

EXAMPLE 1 des-Acetylvinblastine-4-O-(N-Acetyl-4-trans-L-Hyp-Ser-Ser Chg-Gln-Ser-Ser-Pro) ester Step A: Preparation of 4-des- Acetylvinblastine A sample of 2.40 g (2.63 mmol) of vinblastine sulfate (Sigma V-1 377) was dissolved under $N_2$ in 135 ml of absolute methanol and treated with 45 ml of anhydrous hydrazine, and the solution was stiured at 20–25° C. for 18 hr. The reaction was evaporated to a thick paste, which was partitioned between 300 ml of $CH_2Cl_2$ and 150 ml of saturated $NaHCO_3$. The aqueous layer was washed with 2 100-ml portions of $CH_2Cl_2$, and each of the 3 $CH_2Cl_2$ layers in turn was washed with 100 ml each of $H_2O$ (2X) and saturated NaCl (iX). The combined organic layers were dried over anhydrous Na2SO4, and the solvent was removed at reduced pressure to yield the title compound as an off-white crystalline solid. This material was stored at -20° C until use.

Step B: Preparation of 4-des- Acetylvinblastine 4-O-(Prolyl) ester

A sample of 804 mg (1.047 mmol) of 4-des-acetylvinblastine, dissolved in 3 ml of $CH_2CI2$ and 18 ml of anhydrous pyridine under nitrogen, was treated with 1.39 g of Fmoc-proline acid chloride (Fmoc-Pro-Cl, Advanced Chemtech), and the mixture was stirred for 20 hr at 25° C. When analysis by HPLC revealed the presence of unreacted starting des- acetylvinblastine, another 0.50 g of Fmoc-Pro–Cl was added, with stirring another 20 hr to complete the reaction. Water (ca. 3 ml) was added to react with the excess acid chloride, and the solution was then evaporated to dryness and partitioned between 300 ml of EtOAc and 150 ml of saturated $NaHCO_3$, followed by washing twice with saturated NaCl. After drying ($Na_2SO_4$), the solvent was removed under reduced pressure to give an orange-brown residue, to which was added 30 ml of DMF and 14 ml of piperidine, and after 5 min the solution was evaporated under reduced pressure to give a orange-yellow semi-solid residue. After drying in vacuo for about 1 hr, approx. 200 ml of $H_2O$ and 100 ml of ether was added to this material, followed by glacial HOAc dropwise with shaking and sonication until complete dissolution had occurred and the aqueous layer had attained a stable pH of 4.5–5.0 (moistened pH range 4–6 paper). The aqueous layer was then washed with 1 100-mi portion of ether, and each ether layer was washed in turn with 50 ml of $H_2O$. The combined aqueous layers were subjected to preparative HPLC in 2 portions on a Waters $C_4$ Delta-Pak column 15RM 300A (A=0.1% TFA/

H₂O; B=0.1% TFA/CH₃CN), gradient elution 95 -->70% A/ 70 min. Pooled fractions yielded, upon concentration and lyophilization, the title compound.

Step C: N-Acetyl-4-trans-L-Hyp-Ser-Ser Chg-Gln-Ser-Ser-WANG Resin

Starting with 0.5 mmole (0.61 g) of Fmoc-Ser(t-Bu)-WANG resin loaded at 0.82 mmol/g, the protected peptide was synthesized on a ABI model 430A peptide synthesizer adapted for Fmoc/t-butyl-based synthesis. The protocol used a 2-fold excess (1.0 ummol) of each of the following protected amino acids: Fmoc-Ser (t-Bu)-OH, Fmoc-Gln-OH, Fmoc-Chg-OH, Fmoc-4-trans-L-Hyp-OH; and acetic acid (double coupling). During each coupling cycle Fmoc protection was removed using 20% piperidine in N-methyl-2-pyrrolidinone (NMP), followed by washing with NMP. Coupling was achieved using DCC and HOBt activation in NMP. At the completion of the synthesis, the peptide resin was dried to yield the title compound.

Step D: N-Acetyl-4-trans-L-Hyp-Ser-Ser Chg-Gln-Ser-Ser-OH

One 0.5-mmol run of the above peptide-resin was suspended in 25 ml of TFA, followed by addition of 0.625 ml each of H₂O and triisopropylsilane, then stirring at 25° for 2.0 hr. The cleavage mixture was filtered, the solids were washed with TFA, the solvents were removed from the filtrate under reduced pressure, and the residue was triturated with ether to give a pale yellow solid, which was isolated by filtration and drying in vacuo to afford the title compound.

HPLC conditions, system A:

Column . . . Vydac 15 cm #218TP5415, C18

Eluant . . . Gradient (95%A -->50%A) over 45 min. A=0.1% TFA/H₂O, B=0.1% TFA/acetonitrile Flow . . . 1.5 ml/min.

High Resolution ES/FT-MS: 789.3

Step E: des- Acetylvinblastine-40-(N-Acetyl-4-trans-L-Hyp-Ser-Ser Chg-Gln-Ser-Ser-Pro) ester Samples of 522 mg (0.66 mmol) of the peptide from step D and 555 mg (ca. 0.6 mmol) of 4-des- Acetylvinblastine 4-0-(Prolyl) ester from Step B, prepared as above, were dissolved in 17 ml of DMF under N₂. Then 163 mg (1.13 mmol) of 1-hydroxy-7-azabenzotriazole (HOAt) was added, and the pH was adjusted to 6.5–7 (moistened 5–10 range pH paper) with 2,4,6-collidine, followed by cooling to 0° C. and addition of 155 mg (0.81 mnuol) of 1-(3-dimethylaminopropyl)-3-ethylcarbodiimide hydrochloride (EDC). Stirring was continued at 0–5° C. until completion of the coupling as monitored by analytical HPLC (A=0.1% TFA/H₂O; B=0.1% TFA/CH₃CN), maintaining the pH at 6.5–7 by periodic addition of 2,4,6-collidine. After 12 hr the reaction was worked up by addition of ~4 ml of H₂O and, after stirring 1 hr, concentrated to a small volume in vacuo and dissolution in ca. 150 ml of 5% HOAc. and preparative HPLC in two portions on a Waters C₁₈ Delta-Pak column 15μM 300A (A=0.1% TFA/H20; B=0.1% TFAICH₃CN), gradient elution 95 -->65% A / 70 min). Homogeneous fractions containing the later-eluting product (evaluated by HPLC, system A, 95 -->65% A / 30 min) from both runs were pooled and concentrated to a volume of 50 ml and passed through approx. 40 ml of AG4X4 ion exchange resin (acetate cycle), followed by freeze-drying to give the title compound as a lyophilized powder.

High Resolution ES/FT-MS: 1637.0

EXAMPLE 1A des-Acetylvinblastine-4-O-(N-Acetyl-4-trans-L-Hyp-Ser-Ser Chg-Gln-Ser-Ser-Pro) ester acetate A sample of 4.50 g (3.7 mmol) of 4-O-(prolyl) des-acetylvinblastine TWA salt, prepared as described in Example 1, Step B, was dissolved in 300 ml of DMF under N₂, and the solution was cooled to 0°. Then 1.72 g (10.5 mmol) of 3,4-dihydro-3-hydroxy-4-oxo-1,2,3-benzotriazine (ODHBT) was added, and the pH was adjusted to 7.0 (moistened 5–10 range pH paper) with N-methylmorpholine (NMM), followed by the addition of 4.95 g (5.23 nmol) of the N-acetyl-heptapeptide of Example 1, Step D, portionwise allowing complete dissolution between each addition. The pH was again adjusted to 7.0 with NMM, and 1.88 g (9.8 mmol) of 1-(3-dimethylaminopropyl)-3-ethylcarbodiimide hydrochloride (EDC) was added, followed by stirring of the solution at 0–5° C. until completion of the coupling as monitored by analytical HPLC (system A), maintaining the pH at ca. 7 by periodic addition of NMM. The analysis showed the major component at 26.3 min retention time preceded by a minor component (ca. 10 %) at 26.1 min, identified as the D-Ser isomer of the title compound. After 20 hr the reaction was worked up by addition of 30 ml of H₂O and, after stirring 1 hr, concentrated to a small volume in vacuo and dissolution in ca. 500 ml of 20% HOAc. and preparative HPLC in 12 portions on a Waters C18 Delta-Pak column 15mM 300A (A =0.1 % TFA/H₂O; B=0.1% TFA/CH₃CN), gradient elution 85 -->65% A / 90 min) at a flow rate of 80 ml/min.

Homogeneous fractions (evaluated by HPLC, system C) representing approx. one-fourth of the total run were pooled and concentrated to a volume of 150 ml and passed through approx. 200 ml of Bio-Rad AG4X4 ion exchange resin (acetate cycle), followed by freeze-drying of the eluant gave the acetate salt of the title compound as a lyophilized powder: retention time (system A) 26.7 min, 98.9% pure; high resolution ES/FT-MS m/e 1636.82; amino acid compositional analysis 20 hr, 100° C., 6N HCl (theory/found), Ser4/3.91 (corrected), Glu 1/0.92 (Gln converted to Glu), Chg 1/1.11, Hyp 1/1.07, Pro 1/0.99, peptide content 0.516 mmol/mg.

Further combination of homogeneous fractions and purification from side fractions, processing as above through approx. 500 ml of ion exchange resin, afforded an additional amounts of the title compound.

HPLC conditions, system A:

Column . . . Vydac 15 cm #218TP5415, C₁₈

Flow . . . 1.5 ml/min.

Eluant . . . Gradient (95%A -->50%A) over 45 min.

A=0.1% TFA/H₂O, B=0.1% TFA/acetonitrile

Wavelenth . . . 214 nm, 280 nm

HPLC conditions, system C:

Column . . . Vydac 15 cm #218TP5415, C18

Flow . . . 1.5 ml/min.

Eluant . . . Gradient (85%A -->65%A) over 30 min.

A=0.1% TFA/H₂O, B=0.1% TFA/acetonitrile

Wavelenth . . . 214nm, 280 nm

Table 1 shows other peptide-vinca drug conjugates that were prepared by the procedures described in Examples 1 and 1A, but utilizing the appropriate amino acid residues and blocking group acylation. Unless otherwise indicated, the acetate salt of the conjugate was prepared and tested.

TABLE 1

| SEQ ID.NO. | PEPTIDE-VIN CONJUGATE | Time to 50% Substrate Cleavage by York PSA (Min) |
|---|---|---|
| 95 | 4-O-(Ac-4-trans-L-HypSSChgQ-SS-4-trans-L-Hyp)-dAc-VIN | 13 |
| 96 | 4-O-(Ac-4-trans-L-HypSSChgQ-S-P)-dAc-VIN | 1 HOUR = 8% |
| 90 | 4-O-(Ac-Abu-SSChgQ-SP)-dAc-VIN | 80 |
| 91 | 4-O-((2-OH)Ac-Abu-SSChgQ-S-P)-dAc-VIN | 110 |
| 92 | 4-O-(Ac-3-Pal-SSChgQS-P)-dAc-VIN | 80 |
| 97 | 4-O-(Ac-3-Pal-SSChgQ(dS)-P)-dAc-VIN | 3 HOURS = 0% |
| 93 | 4-O-(Ac-4-trans-L-HypSSChgQSL-lactyl)-dAc-VIN | 10 (slight degradation) |
| 94 | 4-O-(Ac-4-trans-L-HypSSChgQSV-lactyl)-dAc-VIN | 7 (stable) |
| 88 | 4-O-(Ac-4-trans-L-HypSSChgQSV-glycolyl)-VIN | 8 |
| 85 | 4-O-(Ac-4-trans-L-HypSSChgQS-Glycine)-(dAc)-VIN | 30 |
| 86 | 4-O-(Ac-4-trans-L-HypSSChgQSS-Sar)-(dAc)-VIN | 32 |
| 84 | 4-O-(Ac-4-trans-L-HypSSChgQSSPro)-(dAc)-VIN | 17 |
| 87 | 4-O-(Ac-4-trans-L-HypSSChgQSS-(d)-Pro)-(dAc)-VIN | 1 HOUR = 34% |
| 98 | 4-O-(Ac-SSChgQS-Gly)-(dAc)-VIN | 55 |
| 99 | 4-O-(Ac-SSChgQ-SS-4-trans-L-Hyp)-dAc-VIN | 22 |
| 100 | 4-O-(Ac-SSChgQ-SS-P)-dAc-VIN | 15 |
| 101 | 4-O-(Ac-4-trans-L-HypSSChgQ-S(dS)-4-trans-L-Hyp)-dAc-VIN | 1 HOUR = 12% |
| 102 | (4-O)-Ac-(4-trans-L-Hyp)SSChgQ-SL-(dAc)-VIN | 35 |
| 103 | Ac-4-trans-L-HypSSChgQS-(4-O-Ala)-(dAc)-VIN | 23 (prod converts to 4-O-A-dAc-VIN) |
| 104 | Ac-4-trans-L-HypSSChgQSChg-(4-O-glycolyl)-VIN | 12 |
| 105 | Ac-4-trans-L-HypSSChgQSS-(4-O-Sar)-(dAc)-VIN | 15 |
| 102 | 4-O-(Ac-4-trans-L-HypSSChgQSL-lactyl)-(dAc)-VIN | 10 |
| 106 | Ac-SSChgQ-SS-(4-O-4-trans-L-Hyp)-dAc-VIN | 22 |
| 107 | Ac-4-trans-L-HypSSChgQ-SS(4-O-P)-Vindesine | 12 |
| 108 | Ac-AbuSSChgQ-S(ds)-(4-O-P)-dAc-VIN | 60 |
| 109 | Ac-AbuSSChgQ-SS-(4-O-P)-dAc-VIN | 7 |
| 110 | Ac-AbuSSChgQ-(dS)-(4-O-P)-dAc-VIN | 1 HOUR = 0% |
| 104 | Ac-4-trans-L-HypSSChgQ-SChg-(4-O-lactyl)-dAc-VIN | 14 |
| 111 | Ac-SSChgQ-SS-(4-O-P)-Vindesine | 22 |
| 112 | 4-O-[Ac-SSChgQ-S(dS)- 4-trans-L-Hyp]-dAc-VIN | 1 HOUR = 14% |

TABLE 1-continued

| SEQ ID.NO. | PEPTIDE-VIN CONJUGATE | Time to 50% Substrate Cleavage by York PSA (Min) |
|---|---|---|
| 113 | 4-O-[Ac-4-trans-L-HypSSChgQ-(dS)SP]-dAc-VIN | 6 HOURS (10 X ENZ) |
| 114 | 4-O-[Ac-4-trans-L-HypSSChg(dQ)SSP]-dAc-VIN | 10 X ENZ o/n = 0% |
| 115 | 4-O-[Ac-4-trans-L-HypSSChg(dQ)(dS)SP]-dAc-VIN | 10 X ENZ o/n = 0% |
| 116 | 4-O-(Ac-SChgQ-SSP)-dAc-VIN | 15 |
| 117 | 4-O-[Ac-SChgQSS4-trans-L-Hyp]-dAc-VIN | 15 |
| 118 | 4-O-[Ac--SChgQSS-Sar]-dAc-VIN | 39 n = 2 |
| 119 | 4-O-[Ac-SChgQSS-AiB-P]-dAc-VIN | 15, 23 |
| 120 | 4-O-[Ac-SChgQSS(N-Me-Ala)]-dAc-VIN | 30 |
| 121 | 4-O-[Ac-SChgQS-Aib-P]-dAc-VIN | 1 HOUR = 8% |
| 122 | 4-O-[(2-OH)Ac-SchgQSS-Sar]-dAc-VIN | 1 HOUR = 4% |
| 123 | 4-O-[Ac-SChgQSS-Pip]-dAc-VIN | 15 |
| 124 | 4-O-[Ac-4-trans-L-HypSSChgQSS-Pip]-dAc-VIN | 13 |
| 125 | 4-O-[Ac-SChgQSS-(N-Me-dA)]-dAc-VIN | 1 HOUR = 26% |

4-trans-L-Hyp is trans-4-hydroxy-L-proline
when n > 1; value is an average

EXAMPLE 4

Assessment of the Recognition of Oligopeptide- Vinca Drug Conjugates by Free PSA The conjugates prepared as described in Example 3 were individually dissolved in PSA digestion buffer (50 mM tris(hydroxymethyl)-aminomethane pH7.4, 140 mM NaCl) and the solution added to PSA at a molar ration of 100 to 1. Alternatively, the PSA digestion buffer utilized is 50 mM tris(hydroxymethyl)-aminomethane pH7.4, 140 mM NaCl. The reaction was quenched after various reaction times by the addition of trifluoroacetic acid (TFA) to a final 1% (volume/volume). Alternatively the reaction is quenched with 10 mM $ZnCl_2$. The quenched reaction was analyzed by HPLC on a reversed-phase C18 column using an aqueous 0.1%TFA/acetonitrile gradient. The amount of time (in minutes) required for 50% cleavage of the noted oligopeptide-cytotoxic agent conjugates with enzymatically active free PSA were then calculated. The results are shown in Table 1.

EXAMPLE 5

In vitro Assay of Cytotoxicity of Peptidyl Derivatives of Vinca Drugs

The cytotoxicities of the cleaveable oligopeptide-vinca drug conjugates, prepared as described in Example 3, against a line of cells which is known to be killed by unmodified vinca drug was assessed with an Alamar Blue assay. Specifically, cell cultures of LNCap prostate tumor cells, Colo320DM cells (designated $C_{320}$) or T47D cells in 96 well plates was diluted with medium containing various concentrations of a given conjugate (final plate well volume of 200 µl). The Colo320DM cells, which do not express free PSA, are used as a control cell line to determine non-mechanism based toxicity. The cells were incubated for 3 days at 37° C., 20 µl of Alamar Blue is added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures and an $EC_{50}$ was determined. The results are shown in Table 2. Unless otherwise indicated, the acetate salt of the conjugate was tested.

TABLE 2

| SEQ.ID NO. | PEPTIDE-VIN CONJUGATE (Cytotoxic Agent) | LNCaP Cell Kill in 72 HRS. {48 HRS} EC 50 (µM) |
|---|---|---|
|  | VINBLASTINE | 0.5 (Colo320DM = 0.5) |
|  | (4-O-4-trans-L-Hyp)-dAc-VIN | 0.6 (Colo320DM = 1.1)n = 2 |

TABLE 2-continued

| SEQ.ID NO. | PEPTIDE/PEPTIDE-VIN CONJUGATE | LNCaP Cell Kill in 72 HRS. {48 HRS} EC 50 (mM) |
|---|---|---|
| | 4-O-glycine-(dAc)-VIN | 0.3 (Colo320DM = 1.8) |
| | 4-O-sarcosyl-(dAc)-VIN | 1.3 (Colo320DM = 1.8) |
| 95 | 4-O-(Ac-4-trans-L-HypSSChgQ-SS-4-trans-L-Hyp)-dAc-VIN | 16.3 (Colo320DM = 13.1) |
| 96 | 4-O-(Ac-4-trans-L-HypSSChgQ-S-P)-dAc-VIN | 47.9 (Colo320DM = 83.9) |
| 96 | 4-O-(Ac-4-trans-L-Hyp SSChgQS-Pro)-(dAc)-VIN | >16 (Colo320DM = 26) in 5% FBS |
| 90 | 4-O-(Ac-Abu-SSChgQ-S-P)-dAc-VIN | 9.7 (Colo320DM = 14.5) n = 2 |
| 90 | " | >5(Colo320DM = 23.8) in 0.5% FBS |
| 91 | 4-O-((2-OH)Ac-Abu-SSChgQ-S-P)-dAc-VIN | 11.9 (Colo320DM = 52.5) |
| 92 | 4-O-(Ac-3-Pal-SSChgQS-P)-dAc-VIN | 5.8 (Colo320DM = 8.0)PS |
| 93 | 4-O-(Ac-4-trans-L-Hyp SSChgQSL-lactyl)-dAc-VIN | 1.1 (Colo320DM = 13.3) |
| 94 | 4-O-(Ac-4-trans-L-Hyp SSChgQSV-lactyl)-dAc-VIN | 3.1 (Colo320DM = 8.1) |
| 88 | 4-O-(Ac-4-trans-L-HypS SChgQSV-glycolyl)-VIN | 4.1 (Colo320DM = 8.1) |
| 86 | 4-O-(Ac-4-trans-L-Hyp SSChgQSS-Sar)-(dAc)-VIN | 4.1 (Colo320DM = 13.0) |
| 84 | 4-O-(Ac-4-trans-L-Hyp SSChgQSSPro)-(dAc)-VIN | 3.0 (Colo320DM = 12) n = 3 |
| 87 | 4-O-(Ac-4-trans-L-Hyp SSChgQSS-(d)-Pro)-(dAc)-VIN | 4.1 (Colo320DM = 8.1) |
| 85 | 4-O-(Ac-4-trans-L-Hyp SSChgQSGly)-(dAc)-VIN | 9.3 (Colo320DM = 13.5) n = 2 |
| 98 | 4-O-(Ac-SSChgQS-Gly)-(dAc)-VIN | 16.3 (Colo320DM = 16.3) |
| 100 | 4-O-(Ac-SSChgQ-SS-4-trans-L-Hyp)-dAc VIN | 6.8 (Colo320DM = 8.1) n = 2 |
| SEQ.ID NO. | PEPTIDE/PEPTIDE-VIN CONJUGATE | LNCaP Cell Kill in 72 HRS. {48 HRS} EC 50 (mM) |
| | 4-O-leucyl-(dAc)-VIN | 4.5 (Colo320DM = 4.5) |
| | 4-O-Abu-(dAc)-VIN, racemic mixture | 3.8 (Colo320DM = 5.5) |
| | 4-O-Abu-(dAc)-VIN, I isoform | 3.9 (Colo320DM = 2.3) |
| 102 | (4-O)-Ac-(4-trans-L-Hyp)SSChgQ-SL-(dAc) VIN | 40 (Colo320DM = 86.7)SF; 50 (97) 0.5% FBS |
| | 4-O-(prolyl)-dAc-VIN | 0.7(Colo320DM = 4.1) n = 2 |
| | (4-O-Phe)-(dAc)-VIN | 3.8 (Colo320DM = 2.2) |
| | (4-O-Ala)-(dAc)-VIN | 0.6 (Colo320DM = 4.2) |

TABLE 2-continued

| | | |
|---|---|---|
| 103 | Ac-4-trans-L-HypSSChgQS-(4-O-Ala)-(dAc)-VIN | 12.5 (Colo320DM = 32.5) |
| | 4-hydroxyacetyl-VIN = 4-O-glycolyl-dAc-VIN | 1.3 (Colo320DM = 3.3) |
| 104 | Ac-4-trans-L-HypSSChgQSChg-(4-O-glycolyl)-VIN | 4.1 (Colo320DM = 4.1) |
| | 4-O-(d)-prolyl-(dAc)-VIN ester | 2.0 (Colo320DM = 4.1) |
| | Chg-(4-O-Glycolyl)-VIN | |
| 105 | Ac-4-trans-L-HypSSChgQSS-(4-O-Sar)-(dAc)-VIN | 12 (Colo320DM = 12) |
| 102 | 4-O-(Ac-4-trans-L-HypSSChgQSL-lactyl)-(dAc)-VIN | 1.1 (Colo320DM = 13.3) |
| | 4-O-(V-lactyl)-dAc-VIN | 1.3 (Colo320DM = 2.6) |
| | 4-O-(L-lactyl)-dAc-VIN | 0.7 (Colo320DM = 2.0) |
| | 4-O-(Chg-lactyl)-dAc-VIN | 4.1 (Colo320DM = 8.4) |
| 104 | 4-O-(Ac-4-trans-L-HypSSChgQSChg-lactyl)-dAc-VIN | 8.1 (Colo320DM = 27.9) PS |
| 106 | Ac-SSChgQ-SS-(4-O-Hyp)-dAc-VIN | 6.8 (Colo320DM = 8.1) n = 2 |
| 107 | Ac-4-trans-L-HypSSChgQ-SS(4-O-P)-Vindesine | 12.5 (Colo320DM > 73) |
| 108 | Ac-AbuSSChgQ-SS-(4-O-P)-dAc-VIN | 12.8 (Colo320DM = 28.4) |
| | Prolyl-Vindesine | 0.3 (Colo320DM = 6.9) |
| 111 | Ac-SSChgQ-SS-(4-O-P)-Vindesine | 32.5 (Colo320DM > 73) |
| | 4-O-(SP)-dAc-VIN | 0.1 (Colo320DM = 0.3) |
| | 4-O-(SSP)-dAc-VIN | 2.0 (Colo320DM = 14.5) |
| 114 | 4-O-[Ac-4-trans-L-HypSSChg(dQ)SSP]-dAc-VIN | 12.2 (Colo320DM = 43.7) |
| 115 | 4-O-[Ac-4-trans-L-HypSSChg(dQ)(dS)SP]-dAc-VIN | 16.3 (Colo320DM = 47.7) |
| 116 | 4-O-(Ac-SChgQ-SSP)-dAc-VIN | 15 (Colo320DM = 20) |
| | 4-O-pipecolyl-dAc-VIN | 0.7 (Colo320DM = 0.7) |
| 117 | 4-O-[Ac-SChgQSS4-trans-L-Hyp]-dAc-VIN | 5.6 (Colo320DM = 5.6) |
| | 4-O-N-methylalanyl-dAc-VIN | 2.9 (Colo320DM = 2.9) |
| 118 | 4-O-[Ac--SChgQSS-Sar]-dAc-VIN | 0.8 (Colo = 3.0) |
| 119 | 4-O-[Ac-SChgQSS-Aib-P]-dAc-VIN | > 25(Colo320DM > 25) |
| 120 | 4-O-[Ac-SChgQSS(N-Me-Ala)]-dAc-VIN | 2.3 (Colo320DM = 3.1) |

TABLE 2-continued

| 123 | 4-O-[Ac-SChgQSS-Pip]-dAc-VIN | 80 (Colo320DM > 75) |
|---|---|---|
| 124 | 4-O-[Ac-4-trans-L-HypSSChgQSS-Pip]-dAc-VIN | 7.5 (Colo320DM = 60) |
|  | 4-O-[N-Me-dA]-dAc-VIN | 1.0 (Colo320DM = 1.7) |

Pip is pipecolinic acid; Sar is sarcosine; Chg is cyclohexylglycine; Abu is 2-aminobutyric acid; Aib is 2-aminoisobutyric acid.

EXAMPLE 6
In vivo Efficafy of Peptidel –Cytotoxic Agent Conjugates

LNCaP.FGC or DuPRO-1 cells are trypsinized, resuspended in the growth medium and centifuged for 6 mins. at 200xg. The cells are resuspended in serum-free a-MEM and counted. The appropriate volume of this solution containing the desired number of cells is then transferred to a conical centrifuge tube, centrifuged as before and resuspended in the appropriate volume of a cold 1:1 mixture of α-MEM-Matrigel. The suspension is kept on ice until the animals are inoculated.

Harlan Sprague Dawley male nude mice (10–12 weeks old) are restrained without anesthesia and are inoculated with 0.5 mL of cell suspension on the left flank by subcutaneous injection using a 22G needle. Mice are either given approximately $5\times10^5$ DuPRO cells or $1.5\times10^7$ LNCaP.FGC cells.

Following inoculation with the tumor cells the mice are treated under one of two protocols:

Protocol A:

One day after cell inoculation the animals are dosed with a 0.1–0.5 mL volume of test conjugate, vinca drug or vehicle control (sterile water). Dosages of the conjugate and vinca drug are initially the maximum non-lethal amount, but may be subsequently titrated lower. Identical doses are administered at 24 hour intervals for 5 days. After 10 days, blood samples are removed from the mice and the serum level of PSA is determined. Similar serum PSA levels are determined at 5–10 day intervals. At the end of 5.5 weeks the mice are sacrificed and weights of any tumors present are measured and serum PSA again determined.The animals' weights are determined at the beginning and end of the assay.

Protocol B:

Ten days after cell inoculation,blood samples are removed from the animals and serum levels of PSA are determined. Animals are then grouped according to their PSA serum levels. At 14–15 days after cell inoculation, the animals are dosed with a 0.1–0.5 mL volume of test conjugate, vinca drug or vehicle control (sterile water). Dosages of the conjugate and vinca drug are initially the maximum non-lethal amount, but may be subsequently titrated lower. Identical doses are administered at 24 hour intervals for 5 days. Serum PSA levels are determined at 5–10 day intervals. At the end of 5.5 weeks the mice are sacrificed, weights of any tumors present are measured and serum PSA again determined. The animals' weights are determined at the beginning and end of the assay.

EXAMPLE 7
In vitro determination of proteolytic cleavage of conjugates by endogenous non-PSA proteases Step A: Preparation of proteolvtic tissue extracts All procedures are carried out at 4° C. Appropriate animals are sacrificed and the relevant tissues are isolated and stored in liquid nitrogen. The frozen tissue is pulverized using a mortar and pestle and the pulverized tissue is transfered to a Potter-Elvejeh homogenizer and 2 volumes of Buffer A (50 mM Tris containing 1.15% KCI, pH 7.5) are added. The tissue is then disrupted with 20 strokes using first a lose fitting and then a tight fitting pestle. The homogenate is centrifuged at 10,000× g in a swinging bucket rotor (HB4–5), the pellet is discarded and the re-supematant centrifuged at 100,000× g (Ti 70). The supernatant (cytosol) is saved.

The pellet is resuspended in Buffer B (10 mM EDTA containing 1.15% KCl, pH 7.5) using the same volume used in step as used above with Buffer A. The suspension is homogenized in a dounce homogenizer and the solution centrifuged at 100,000× g. The supernatant is discarded and the pellet resuspended in Buffer C(10 mM potassium phosphate buffer containingO.25 M sucrose, pH 7.4), using ½ the volume used above, and homogenized with a dounce homogenizer.

Protein content of the two solutions (cytosol and membrane) is determine using the Bradford assay. Assay aliquots are then removed and frozen in liquid $N_2$. The aliquots are stored at –70° C.

Step B: Proteolytic cleavage assay

For each time point, 20 microgram of peptide-vinca drug conjugate and 150 micrograms of tissue protein, prepared as described in Step A and as determined by Bradford in reaction buffer are placed in solution of final volume of 200 microliters in buffer (50 mM TRIS, 140 mM NaCl, pH 7.2). Assay reactions are run for 0, 30, 60, 120, and 180 minutes and are then quenched with 9 microliters of 0.1 M $ZnCl_2$ and immediately placed in boiling water for 90 seconds. Reaction products are analyzed by HPLC using a VYDAC C18 15 cm column in water I acetonitrile (5% to 50% acetonitrile over 30 minutes).

What is claimed is:

1. A conjugate of the formula I:

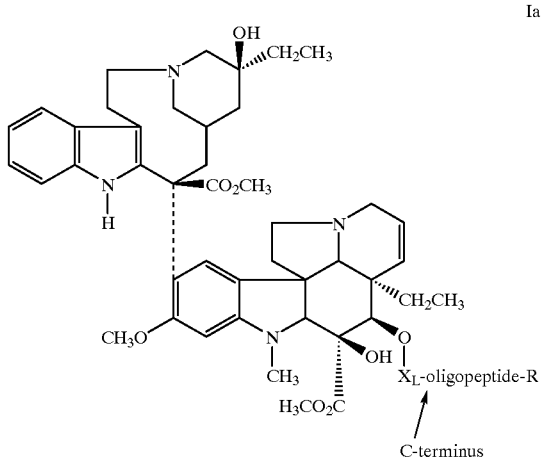

wherein: oligopeptide is an oligopeptide which is specifically recognized by the free prostate specific antigen (PSA) and is capable of being proteolytically cleaved by the enzymatic activity of the free prostate specific antigen, $X_L$ is a bond
R is selected from
a) hydrogen,
b) —(C=O)$R^{1a}$, c) 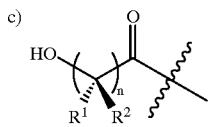

d) 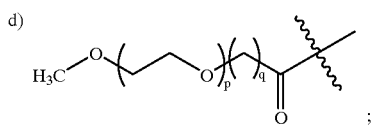

e) 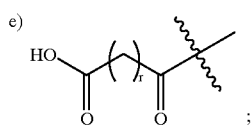

f) ethoxysquarate; and
g) cotininyl;

$R^1$ and $R^2$ are independently selected from: hydrogen, OH, $C_1$-$C_6$ alkyl, $C_1$-$C_6$ alkoxy, $C_1$-$C_6$ aralkyl and aryl;
$R^{1a}$ is $C_1$-$C_6$-alkyl, hydroxylated $C_3$-$C_8$-cycloaLkyl, polyhydroxylated $C_3$-$C_8$-cycloalkyl, hydroxylated aryl, polyhydroxylated aryl or aryl,
$R^9$ is hydrogen, ($C_1$-$C_3$ alkyl)—CO, or chlorosubstituted ($C_1$-$C_3$ alkyl)—CO;
W is selected from a branched or straight chain $C_1$-$C_6$-alkyl, cyclopentyl, cyclohexyl, cycloheptyl or bicyclo[2.2.2]octanyl;
n is 1, 2, 3 or 4;
p is zero or an integer between 1 and 100;
q is 0 or 1, provided that if p is zero, q is 1;
r is 1, 2 or 3;
t is 3 or 4;
u is 0, 1, 2 or 3,
or a pharmaceutically acceptable salt or optical isomer thereof.

2. The conjugate according to claim 1 wherein: oligopeptide is an oligomer that comprises an amino acid sequence selected from:
a) AsnLysIleSerTyrGlnlSer (SEQ.ID.NO.: 1),
b) LysIleSerTyrGlniSer (SEQ.ID.NO.: 2),
c) AsnLysIleSerTyrTyrlSer (SEQ.ID.NO.: 3),
d) AsnLysAlaSerTyrGlnlSer (SEQ.ID.NO.: 4),
e) SerTyrGIniSerSer (SEQ.ID.NO.: 5);
f) LysTyrGInISerSer (SEQ.ID.NO.: 6);
g) hArgTyrGlnlSerSer (SEQ.ID.NO.: 7);
h) hArgChaGlnlSerSer (SEQ.ID.NO.: 8);
i) TyrGIniSerSer (SEQ.ID.NO.: 9);
j) TyrGlnlSerLeu (SEQ.ID.NO.: 10);
k) TyrGInISerNle (SEQ.ID.NO.: 11);
l) ChgGlnISerLeu (SEQ.ID.NO.: 12);
m) ChgGlnISerNle (SEQ.ID.NO.: 13);
n) SerTyrGInISer (SEQ.ID.NO.: 14);
o) SerChgGlnlSer (SEQ.ID.NO.: 15);
p) SerTyrGInISerVal (SEQ.ID.NO.: 16);
q) SerChgGlnISerVal (SEQ.ID.NO.: 17);
r) SerTyrGlnlSerLeu (SEQ.ID.NO.: 18);
s) SerChgGlnlSerLeu (SEQ.ID.NO.: 19);
t) HaaXaaSerTyrGlnlSer (SEQ.ID.NO.: 20);
u) HaaXaaLysTyrGlnlSer (SEQ.ID.NO.: 21);
v) HaaXaahArgTyrGlnlSer (SEQ.ID.NO.: 22);
w) HaaXaahArgChaGlnlSer (SEQ.ID.NO.: 23);
x) HaaTyrGlnlSer (SEQ.ID.NO.: 24);
y) HaaXaaSerChgGlnlSer (SEQ.ID.NO.: 25);
z) HaaChgGlnISer (SEQ.ID.NO.: 26);
wherein Haa is a cyclic amino acid substituted with a hydrophilic moiety, hArg is homoarginine, Xaa is any amino acid, Cha is cyclohexylalanine and Chg is cyclohexylglycine; or an optical isomer thereof.

3. The conjugate according to claim 2 wherein:
Haa is trans-4-hydroxy-L-proline;
or an optical isomer thereof.

4. The conjugate according to claim 1 wherein the oligopeptide - R is selected from:
Ac-4-trans-L-HypSerSerChgGlnSerSerPro; (SEQ.ID.NO.: 84)
Ac-4-trans-L-HypSerSerChgGlnSerGly; (SEQ.ID.NO.: 85)
Ac-4-trans-L-HypSerSerChgGlnSerSerSar; (SEQ.ID.NO.: 86)
Ac-4-trans-L-Hyp-Ser-Ser Chg-Gln-Ser-Ser-Pro; (SEQ.ID.NO.: 87)
Ac-4-trans-L-Hyp-Ser-Ser Chg-Gln-SerVal; (SEQ.ID.NO.: 88)
Ac-4-trans-L-Hyp-Ser-Ser Chg-Gln-Ser-Ser-4-trans-L-Hyp; (SEQ.ID.NO.: 89)
Ac-Abu-Ser-Ser Chg-Gln-Ser-Pro; (SEQ.ID.NO.: 90)
hydroxyacetylAbu-Ser-Ser Chg-Gln-Ser-Pro; (SEQ.ID.NO.: 91) acetyl3-PALSer-Ser Chg-Gln-Ser-Ser-Pro; (SEQ.ID.NO.: 92)
Ac--4-trans-L-Hyp-Ser-Ser Chg-Gln-Ser-Val; (SEQ.ID.NO.: 93)
Ac--4-trans-L-Hyp-Ser-Ser Chg-Gln-Ser-Leu; (SEQ.ID.NO.: 94)
Ac-4-trans-L-HypSerSerChgGlnSerSer4-trans-L-Hyp; (SEQ.ID.NO.: 95)
Ac-4-trans-L-HypSerSerChgGlnSerPro; (SEQ.ID.NO.: 96)
Ac-SerSerChgGlnSerGly; (SEQ.ID.NO.: 98)
Ac-SerSerChgGlnSerSer-4-trans-L-Hyp; (SEQ.ID.NO.: 99)
Ac-SerSerChgGlnSerSerPro; (SEQ.ID.NO.: 100)
Ac-4-trans-L-HypSerSerChgGlnSerAla; (SEQ.ID.NO.: 103)
Ac-4-trans-L-HypSerSerChgGlnSerChg; (SEQ.ID.NO.: 104)

Ac-4-trans-L-HypSerSerChgGlnSerSerSar; (SEQ.ID.NO.: 105)
Ac-SerSerChgGlnSerSerHyp; (SFQ.ID.NO.: 106)
Ac-4-trans-L-HypSerSerChgGlnSerSerPro; (SEQ.ID.NO.: 107)
Ac-AbuSerSerChgGlnSer(dSer)Pro; (SEQ.ID.NO.: 108)
Ac-AbuSerSerChgGlnSerSerPro; (SEQ.ID.NO.: 109)
Ac-SerSerChgGlnSerSerPro; (SEQ.ID.NO.: 111)
Ac-4-trans-L-HypSerSerChg(dGln)SerSerPro; (SEQ.ID.NO.: 114)
Ac-4-trans-L-HypSerSerChg(dGln)(dSer)SerPro; (SEQ.ID.NO.: 115)
Ac-SerChgGln-SerSerPro; (SEQ.ID.NO.: 116)
Ac-SerChgGlnSerSer-4-trans-L-Hyp; (SEQ.ID.NO.: 117)
Ac--SerChgGlnSerSerSar; (SEQ.ID.NO.: 118)
Ac-SerChgGlnSerSerAibPro; (SEQ.ID.NO.: 119)
Ac-SerChgGlnSerSerN-Me-Ala; (SEQ.ID.NO.: 120)
Ac-4-trans-L-HypSerSerChgGlnSerSerPip; (SEQ.ID.NO.: 124) and
Ac-SerChgGlnSerSerN-Me-dA; (SEQ.ID.NO.: 125)
wherein Abu is aminobutyric acid, 4-trans-L-Hyp is 4-trans-L-hydroxyproline, Pip is pipecolinic acid, 3,4-DiHyp is 3,4-dihydroxyproline, 3-PAL is 3-pyridylalanine, Sar is sarcosine and Chg is cyclohexylglycine.

5. The conjugate according to claim 1 which is selected from:

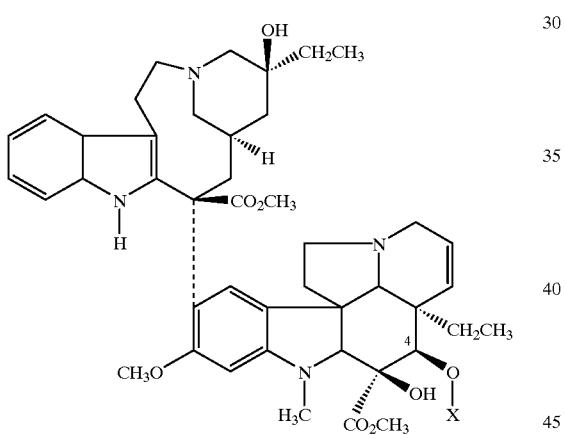

wherein X is

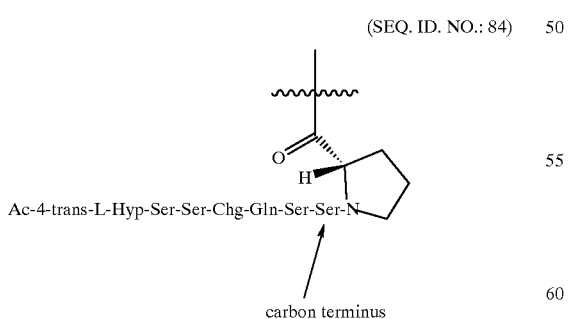

(SEQ. ID. NO.: 84)

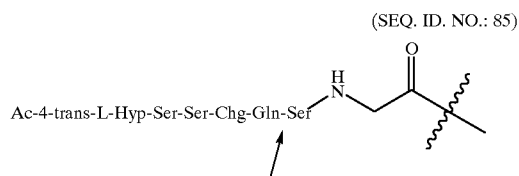

(SEQ. ID. NO.: 85)

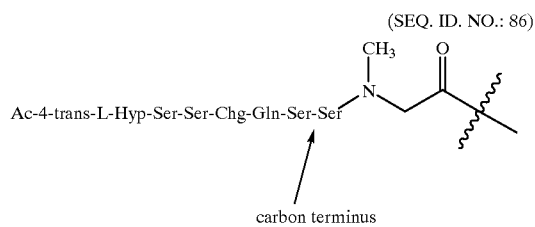

(SEQ. ID. NO.: 86)

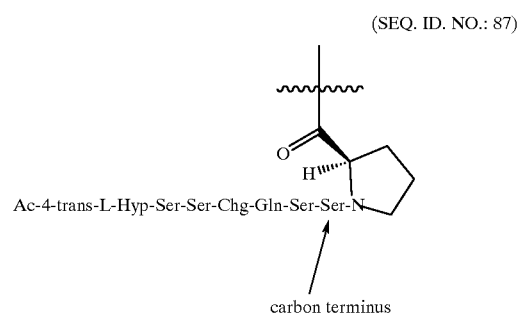

(SEQ. ID. NO.: 87)

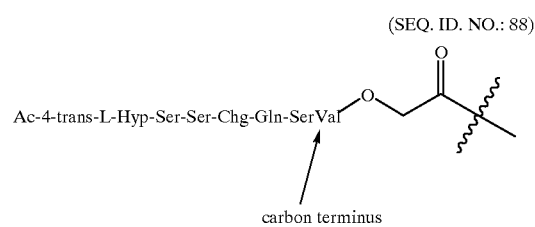

(SEQ. ID. NO.: 88)

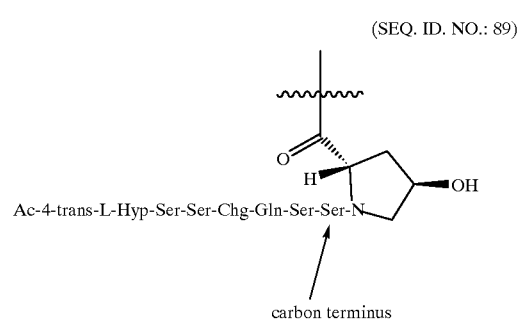

(SEQ. ID. NO.: 89)

-continued (SEQ. ID. NO.: 90)
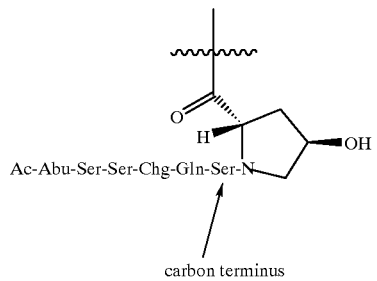
Ac-Abu-Ser-Ser-Chg-Gln-Ser-N
carbon terminus (SEQ. ID. NO.: 91)
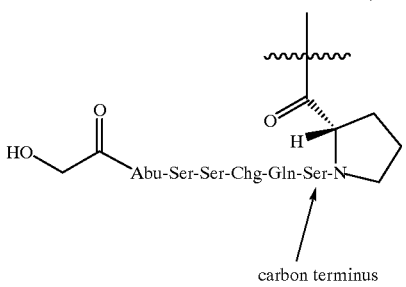
Abu-Ser-Ser-Chg-Gln-Ser-N
carbon terminus (SEQ. ID. NO.: 92)
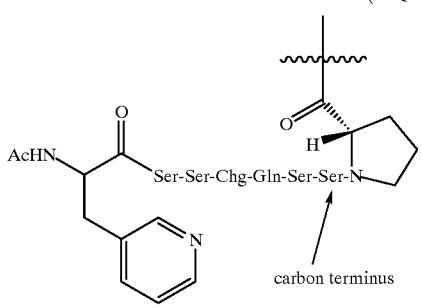
Ser-Ser-Chg-Gln-Ser-Ser-N
carbon terminus (SEQ. ID. NO.: 93)
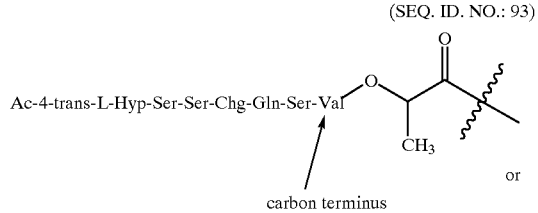
Ac-4-trans-L-Hyp-Ser-Ser-Chg-Gln-Ser-Val
carbon terminus or (SEQ. ID. NO.: 94)
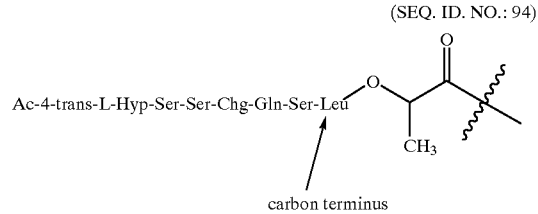
Ac-4-trans-L-Hyp-Ser-Ser-Chg-Gln-Ser-Leu
carbon terminus or a pharmaceutically acceptable salt or optical isomer thereof.

6. The conjugate according to claim 1 which is:

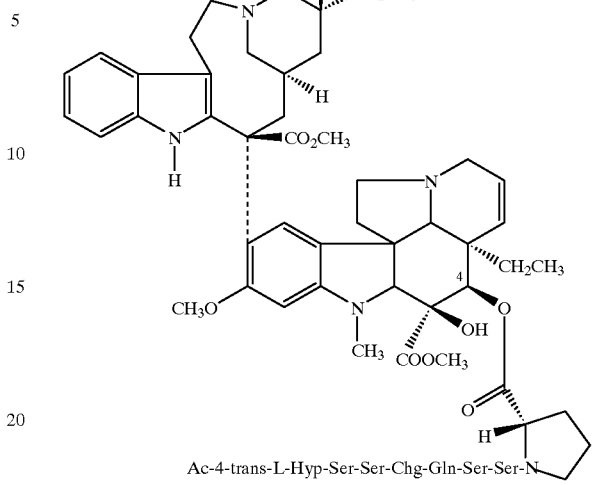
Ac-4-trans-L-Hyp-Ser-Ser-Chg-Gln-Ser-Ser-N or a pharmaceutically acceptable salt or optical isomer thereof.

7. A pharmaceutical composition comprising a pharmaceutical carrier, and dispersed therein, a therapeutically effective amount of a compound of claim 1.

8. A pharmaceutical composition comprising a pharmaceutical carrier, and dispersed therein, a therapeutically effective amount of a conjugate of claim 5.

9. A method for treating prostate cancer which comprises administering to a mammal in need thereof a therapeutically effective amount of a composition of claim 7.

10. A method for treating prostate cancer which comprises administering to a mammal in need thereof a therapeutically effective amount of a composition of claim 8.

11. A method for treating benign prostatic hyperplasia which comprises administering to a mammal in need thereof a therapeutically effective amount of a composition of claim 7.

12. A method for treating benign prostatic hyperplasia which comprises administering to a mammal in need thereof a therapeutically effective amount of a composition of claim 8.

13. A pharmaceutical composition made by combining the conjugate of claim 7 and a pharmaceutically acceptable carrier.

14. A process for making a pharmaceutical composition comprising combining a conjugate of claim 7 and a pharmaceutically acceptable carrier.

* * * * *

UNITED STATES PATENT AND TRADEMARK OFFICE
CERTIFICATE OF CORRECTION

PATENT NO. : 6,174,858 B1
DATED : January 16, 2001
INVENTOR(S) : Stephen F. Brady, Dong-Mei Feng and Victor M. Garsky It is certified that error appears in the above-identified patent and that said Letters Patent is hereby corrected as shown below:

Column 103, claim 1,
Line 27, should read as follows:
-- $X_L$ is a bond; --.
Line 52, should read as follows:
-- $R^{1a}$ is $C_1$-$C_6$-alkyl, hydroxylated $C_3$-$C_8$-cycloalkyl, poly- -- .

Column 104, claim 2,
Lines 4-29, should read as follows:
-- a) AsnLysIleSerTyrGln|Ser (SEQ.ID.NO.: 1),
b) LysIleSerTyrGln|Ser (SEQ.ID.NO.: 2),
c) AsnLysIleSerTyrTyr|Ser (SEQ.ID.NO.: 3),
d) AsnLysAlaSerTyrGln|Ser (SEQ.ID.NO.:4),
e) SerTyrGln|SerSer (SEQ.ID.NO.: 5);
f) LysTyrGln|SerSer (SEQ.ID.NO.: 6),
g) hArgTyrGln|SerSer (SEQ.ID.NO.:7);
h) hArgChaGln|SerSer (SEQ.ID.NO.: 8);
i) TyrGln|SerSer (SEQ.ID.NO.: 9);

j) TyrGln|SerLeu (SEQ.ID.NO.: 10);
k) TyrGln|SerNle (SEQ.ID.NO.: 11);
l) ChgGln|SerLeu (SEQ.ID.NO.: 12);
m) ChgGln|SerNle (SEQ.ID.NO.: 13);
n) SerTyrGln|Ser (SEQ.ID.NO.: 14);
o) SerChgGln|Ser (SEQ.ID.NO.: 15);
p) SerTyrGln|SerVal (SEQ.ID.NO.: 16);
q) SerChgGln|SerVal (SEQ.ID.NO.: 17);
r) SerTyrGln|SerLeu (SEQ.ID.NO.: 18);
s) SerChgGln|SerLeu (SEQ.ID.N0.: 19);
t) HaaXaaSerTyrGln|Ser (SEQ.ID.NO.: 20);
u) HaaXaaLysTyrGln|Ser (SEQ.ID.NO.: 21);
v) HaaXaahArgTyrGln|Ser (SEQ.ID.NO.: 22);
w) HaaXaahArgChaGln|Ser (SEQ.ID.NO.: 23);
x) HaaTyrGln|Ser (SEQ.ID.NO.: 24);
y) HaaXaaSerChgGln|Ser (SEQ.ID.NO.: 25);
z) HaaChgGln|Ser (SEQ.ID.NO.: 26); -- .

UNITED STATES PATENT AND TRADEMARK OFFICE
CERTIFICATE OF CORRECTION

PATENT NO. : 6,174,858 B1  Page 2 of 3
DATED : January 16, 2001
INVENTOR(S) : Stephen F. Brady, Dong-Mei Feng and Victor M. Garsky It is certified that error appears in the above-identified patent and that said Letters Patent is hereby corrected as shown below:

Column 104, claim 4,
Lines 44-57, should read as follows:
-- Ac-4-trans-L-Hyp-Ser-Ser-Chg-Gln-Ser-Ser-Pro; (SEQ.ID.NO.: 87)
Ac-4-trans-L-Hyp-Ser-Ser-Chg-Gln-SerVal; (SEQ.ID.NO.: 88)
Ac-4-trans-L-Hyp-Ser-Ser-Chg-Gln-Ser-Ser-4-trans-L-Hyp; (SEQ.ID.NO.: 89)
Ac-Abu-Ser-Ser-Chg-Gln-Ser-Pro; (SEQ.ID.NO.: 90)
hydroxyacetylAbu-Ser-Ser-Chg-Gln-Ser-Pro; (SEQ.ID.NO.: 91)
acetyl3-PALSer-Ser-Chg-Gln-Ser-Ser-Pro; (SEQ.1D.NO.: 92)
Ac--4-trans-L-Hyp-Ser-Ser-Chg-Gln-Ser-Val; (SEQ.ID.NO.: 93)
Ac--4-trans-L-Hyp-Ser-Ser-Chg-Gln-Ser-Leu; (SEQ.ID.NO.: 94) --.

Column 107, claim 5,
The first structure should be as follows:

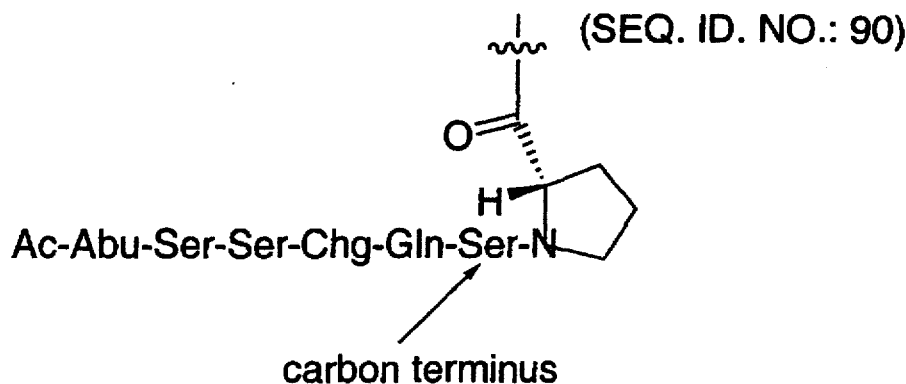

Column 108, claim 7,
Line 29, should read as follows:
-- effective amount of a congugate of claim 1. --.

UNITED STATES PATENT AND TRADEMARK OFFICE
CERTIFICATE OF CORRECTION

PATENT NO.    : 6,174,858 B1
DATED         : January 16, 2001
INVENTOR(S)   : Stephen F. Brady, Dong-Mei Feng and Victor M. Garsky It is certified that error appears in the above-identified patent and that said Letters Patent is hereby corrected as shown below:

Column 105, claim 5,
Between lines 29-46, the structure should be as follows:

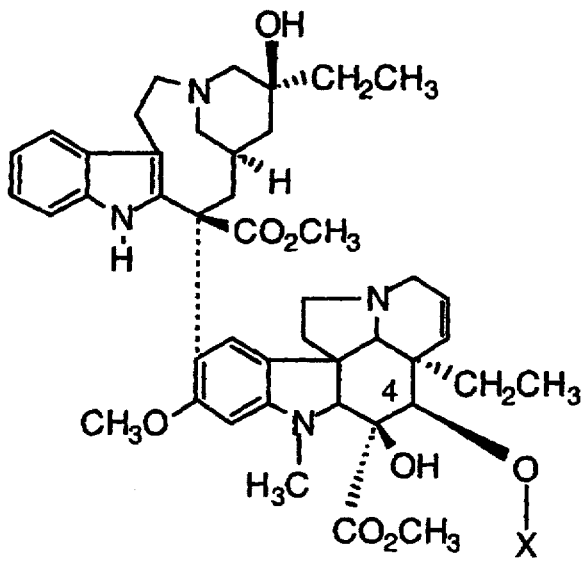

Signed and Sealed this

Twenty-ninth Day of January, 2002

Attest:

JAMES E. ROGAN
*Attesting Officer*  *Director of the United States Patent and Trademark Office*

SEQUENCE LISTING

<160> NUMBER OF SEQ ID NOS: 125

<210> SEQ ID NO 1
<211> LENGTH: 7
<212> TYPE: PRT
<213> ORGANISM: Artificial Sequence
<220> FEATURE:
<223> OTHER INFORMATION: completely synthesized

<400> SEQUENCE: 1

Asn Lys Ile Ser Tyr Gln Ser
 1               5

<210> SEQ ID NO 2
<211> LENGTH: 6
<212> TYPE: PRT
<213> ORGANISM: Artificial Sequence
<220> FEATURE:
<223> OTHER INFORMATION: completely synthesized

<400> SEQUENCE: 2

Lys Ile Ser Tyr Gln Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: completely synthesized

<400> SEQUENCE: 3

Asn Lys Ile Ser Tyr Tyr Ser
 1               5

<210> SEQ ID NO 4
<211> LENGTH: 7
<212> TYPE: PRT
<213> ORGANISM: Artificial Sequence
<220> FEATURE:
<223> OTHER INFORMATION: completely synthesized

<400> SEQUENCE: 4

Asn Lys Ala Ser Tyr Gln Ser
 1               5

<210> SEQ ID NO 5
<211> LENGTH: 5
<212> TYPE: PRT
<213> ORGANISM: Artificial Sequence
<220> FEATURE:
<223> OTHER INFORMATION: completely synthesized

<400> SEQUENCE: 5

Ser Tyr Gln Ser Ser
 1               5

<210> SEQ ID NO 6
<211> LENGTH: 5
<212> TYPE: PRT
<213> ORGANISM: Artificial Sequence
<220> FEATURE:
<223> OTHER INFORMATION: completely synthesized

<400> SEQUENCE: 6

```
Lys Tyr Gln Ser Ser
  1               5

<210> SEQ ID NO 7
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: homoarginine

<400> SEQUENCE: 7

Xaa Tyr Gln Ser Ser
  1               5

<210> SEQ ID NO 8
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: homoarginine
<220> FEATURE:
<221> NAME/KEY: VARIANT
<222> LOCATION: (2)...(2)
<223> OTHER INFORMATION: cyclohexylalanine

<400> SEQUENCE: 8

Xaa Xaa Gln Ser Ser
  1               5

<210> SEQ ID NO 9
<211> LENGTH: 4
<212> TYPE: PRT
<213> ORGANISM: Artificial Sequence
<220> FEATURE:
<223> OTHER INFORMATION: completely synthesized

<400> SEQUENCE: 9

Tyr Gln Ser Ser
  1

<210> SEQ ID NO 10
<211> LENGTH: 4
<212> TYPE: PRT
<213> ORGANISM: Artificial Sequence
<220> FEATURE:
<223> OTHER INFORMATION: completely synthesized

<400> SEQUENCE: 10

Tyr Gln Ser Leu
  1

<210> SEQ ID NO 11
<211> LENGTH: 4
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (4)...(4)
<223> OTHER INFORMATION: Nle
```

```
<400> SEQUENCE: 11

Tyr Gln Ser Leu
1

<210> SEQ ID NO 12
<211> LENGTH: 4
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclohexylglycine

<400> SEQUENCE: 12

Xaa Gln Ser Leu
1

<210> SEQ ID NO 13
<211> LENGTH: 4
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclohexylglycine
<220> FEATURE:
<221> NAME/KEY: MOD_RES
<222> LOCATION: (4)...(4)
<223> OTHER INFORMATION: Nle

<400> SEQUENCE: 13

Xaa Gln Ser Leu
1

<210> SEQ ID NO 14
<211> LENGTH: 4
<212> TYPE: PRT
<213> ORGANISM: Artificial Sequence
<220> FEATURE:
<223> OTHER INFORMATION: completely synthesized

<400> SEQUENCE: 14

Ser Tyr Gln Ser
1

<210> SEQ ID NO 15
<211> LENGTH: 4
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (2)...(2)
<223> OTHER INFORMATION: cyclohexylglycine

<400> SEQUENCE: 15

Ser Xaa Gln Ser
1

<210> SEQ ID NO 16
<211> LENGTH: 5
<212> TYPE: PRT
<213> ORGANISM: Artificial Sequence
<220> FEATURE:
```

```
<223> OTHER INFORMATION: completely synthesized

<400> SEQUENCE: 16

Ser Tyr Gln Ser Val
 1               5

<210> SEQ ID NO 17
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (2)...(2)
<223> OTHER INFORMATION: cyclohexylglycine

<400> SEQUENCE: 17

Ser Xaa Gln Ser Val
 1               5

<210> SEQ ID NO 18
<211> LENGTH: 5
<212> TYPE: PRT
<213> ORGANISM: Artificial Sequence
<220> FEATURE:
<223> OTHER INFORMATION: completely synthesized

<400> SEQUENCE: 18

Ser Tyr Gln Ser Leu
 1               5

<210> SEQ ID NO 19
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (2)...(2)
<223> OTHER INFORMATION: cyclohexylglycine

<400> SEQUENCE: 19

Ser Xaa Gln Ser Leu
 1               5

<210> SEQ ID NO 20
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: UNSURE
<222> LOCATION: (2)...(2)
<223> OTHER INFORMATION: Xaa in this position is any amino acid

<400> SEQUENCE: 20

Xaa Xaa Ser Tyr Gln Ser
 1               5

<210> SEQ ID NO 21
<211> LENGTH: 6
```

```
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: UNSURE
<222> LOCATION: (2)...(2)
<223> OTHER INFORMATION: Xaa in this position is any amino acid

<400> SEQUENCE: 21

Xaa Xaa Lys Tyr Gln Ser
 1               5

<210> SEQ ID NO 22
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: UNSURE
<222> LOCATION: (2)...(2)
<223> OTHER INFORMATION: Xaa in this position is any amino acid
<220> FEATURE:
<221> NAME/KEY: VARIANT
<222> LOCATION: (3)...(3)
<223> OTHER INFORMATION: homoarginine

<400> SEQUENCE: 22

Xaa Xaa Xaa Tyr Gln Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: UNSURE
<222> LOCATION: (2)...(2)
<223> OTHER INFORMATION: Xaa in this position is any amino acid
<220> FEATURE:
<221> NAME/KEY: VARIANT
<222> LOCATION: (3)...(3)
<223> OTHER INFORMATION: homoarginine
<220> FEATURE:
<221> NAME/KEY: VARIANT
<222> LOCATION: (4)...(4)
<223> OTHER INFORMATION: cyclohexylalanine

<400> SEQUENCE: 23

Xaa Xaa Xaa Xaa Gln Ser
 1               5

<210> SEQ ID NO 24
<211> LENGTH: 4
<212> TYPE: PRT
```

```
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophillic moiety

<400> SEQUENCE: 24

Xaa Tyr Gln Ser
 1

<210> SEQ ID NO 25
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: UNSURE
<222> LOCATION: (2)...(2)
<223> OTHER INFORMATION: Xaa in this position is any amino acid
<220> FEATURE:
<221> NAME/KEY: VARIANT
<222> LOCATION: (4)...(4)
<223> OTHER INFORMATION: cyclohexylglycine

<400> SEQUENCE: 25

Xaa Xaa Ser Xaa Gln Ser
 1               5

<210> SEQ ID NO 26
<211> LENGTH: 4
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (2)...(2)
<223> OTHER INFORMATION: cyclohexylglycine

<400> SEQUENCE: 26

Xaa Xaa Gln Ser
 1

<210> SEQ ID NO 27
<211> LENGTH: 6
<212> TYPE: PRT
<213> ORGANISM: Artificial Sequence
<220> FEATURE:
<223> OTHER INFORMATION: completely synthesized

<400> SEQUENCE: 27

Ser Ser Tyr Gln Ser Ala
 1               5

<210> SEQ ID NO 28
<211> LENGTH: 6
<212> TYPE: PRT
```

```
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 28

Ser Ser Xaa Gln Ser Ser
1               5

<210> SEQ ID NO 29
<211> LENGTH: 6
<212> TYPE: PRT
<213> ORGANISM: Artificial Sequence
<220> FEATURE:
<223> OTHER INFORMATION: completely synthesized

<400> SEQUENCE: 29

Ser Ser Tyr Gln Ser Ala
1               5

<210> SEQ ID NO 30
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 30

Ser Ser Xaa Gln Ser Ser
1               5

<210> SEQ ID NO 31
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 31

Pro Ser Ser Tyr Gln Ser
1               5

<210> SEQ ID NO 32
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 32

Pro Ser Ser Xaa Gln Ser
```

```
1               5

<210> SEQ ID NO 33
<211> LENGTH: 6
<212> TYPE: PRT
<213> ORGANISM: Artificial Sequence
<220> FEATURE:
<223> OTHER INFORMATION: completely synthesized

<400> SEQUENCE: 33

Ala Ser Tyr Gln Ser Ser
1               5

<210> SEQ ID NO 34
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 34

Ala Ser Xaa Gln Ser Ser
1               5

<210> SEQ ID NO 35
<211> LENGTH: 6
<212> TYPE: PRT
<213> ORGANISM: Artificial Sequence
<220> FEATURE:
<223> OTHER INFORMATION: completely synthesized

<400> SEQUENCE: 35

Ala Ser Tyr Gln Ser Ala
1               5

<210> SEQ ID NO 36
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 36

Ala Ser Xaa Gln Ser Ala
1               5

<210> SEQ ID NO 37
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 37

Pro Ala Ser Tyr Gln Ser
1               5
```

```
<210> SEQ ID NO 38
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 38

Pro Ala Ser Xaa Gln Ser
  1               5

<210> SEQ ID NO 39
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 39

Ser Ser Xaa Gln Ser Ala Pro
  1               5

<210> SEQ ID NO 40
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 40

Ser Ser Xaa Gln Ser Ser Pro
  1               5

<210> SEQ ID NO 41
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine
<220> FEATURE:
<221> NAME/KEY: MOD_RES
<222> LOCATION: (7)...(7)
<223> OTHER INFORMATION: 4Hyp

<400> SEQUENCE: 41

Ser Ser Xaa Gln Ser Ala Pro
  1               5

<210> SEQ ID NO 42
<211> LENGTH: 7
```

```
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine
<220> FEATURE:
<221> NAME/KEY: MOD_RES
<222> LOCATION: (7)...(7)
<223> OTHER INFORMATION: 4Hyp

<400> SEQUENCE: 42

Ser Ser Xaa Gln Ser Ser Pro
 1               5

<210> SEQ ID NO 43
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: Abu
<220> FEATURE:
<221> NAME/KEY: VARIANT
<222> LOCATION: (4)...(4)
<223> OTHER INFORMATION: cyclohexylglycine

<400> SEQUENCE: 43

Ala Ser Ser Xaa Gln Ser Pro
 1               5

<210> SEQ ID NO 44
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: Abu
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: MOD_RES
<222> LOCATION: (7)...(7)
<223> OTHER INFORMATION: 4Hyp

<400> SEQUENCE: 44

Ala Ser Ser Xaa Gln Ser Pro
 1               5

<210> SEQ ID NO 45
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (4)...(4)
<223> OTHER INFORMATION: cyclohexylglycine

<400> SEQUENCE: 45

Ser Ser Ser Xaa Gln Ser Leu Pro
```

1               5

<210> SEQ ID NO 46
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (4)...(4)
<223> OTHER INFORMATION: cyclohexylglycine

<400> SEQUENCE: 46

Ser Ser Ser Xaa Gln Ser Val Pro
1               5

<210> SEQ ID NO 47
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: MOD_RES
<222> LOCATION: (8)...(8)
<223> OTHER INFORMATION: 4Hyp

<400> SEQUENCE: 47

Ser Ala Ser Xaa Gln Ser Leu Pro
1               5

<210> SEQ ID NO 48
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (4)...(4)
<223> OTHER INFORMATION: cyclohexylglycine

<400> SEQUENCE: 48

Ser Ala Ser Xaa Gln Ser Val Pro
1               5

<210> SEQ ID NO 49
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: METHYLATION
<222> LOCATION: (1)...(1)
<223> OTHER INFORMATION: N.methyl serine
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (8)...(8)
<223> OTHER INFORMATION: pipecolinic acid

<400> SEQUENCE: 49

```
Xaa Ser Ser Xaa Gln Ser Leu Xaa
 1               5
```

<210> SEQ ID NO 50
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: METHYLATION
<222> LOCATION: (1)...(1)
<223> OTHER INFORMATION: N-methyl serine
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (8)...(8)
<223> OTHER INFORMATION: pipecoline

<400> SEQUENCE: 50

```
Xaa Ser Ser Xaa Gln Ser Val Xaa
 1               5
```

<210> SEQ ID NO 51
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 51

```
Pro Ser Ser Tyr Gln Ser Ser Pro
 1               5
```

<210> SEQ ID NO 52
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: MOD_RES
<222> LOCATION: (8)...(8)
<223> OTHER INFORMATION: 4Hyp

<400> SEQUENCE: 52

```
Pro Ser Ser Tyr Gln Ser Ser Pro
 1               5
```

<210> SEQ ID NO 53
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 53

```
Pro Ser Ser Tyr Gln Ser Ser Pro
1               5
```

<210> SEQ ID NO 54
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 54

```
Pro Ser Ser Tyr Gln Ser Ser Ser
1               5
```

<210> SEQ ID NO 55
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: MOD_RES
<222> LOCATION: (8)...(8)
<223> OTHER INFORMATION: 4Hyp

<400> SEQUENCE: 55

```
Pro Ser Ser Tyr Gln Ser Pro
1               5
```

<210> SEQ ID NO 56
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 56

```
Pro Ser Ser Xaa Gln Ser Pro
1               5
```

<210> SEQ ID NO 57
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

```
<400> SEQUENCE: 57

Pro Ser Ser Xaa Gln Ser Ser Pro
1               5

<210> SEQ ID NO 58
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 58

Pro Ser Ser Xaa Gln Ser Leu
1               5

<210> SEQ ID NO 59
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 59

Pro Ser Ser Xaa Gln Ser Val
1               5

<210> SEQ ID NO 60
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 60

Pro Ala Ser Xaa Gln Ser Val Pro
1               5

<210> SEQ ID NO 61
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
```

```
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (8)...(8)
<223> OTHER INFORMATION: pipecolinic acid

<400> SEQUENCE: 61

Pro Ala Ser Xaa Gln Ser Ser Xaa
 1               5

<210> SEQ ID NO 62
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 62

Pro Ser Ser Xaa Gln Ser
 1               5

<210> SEQ ID NO 63
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 63

Pro Ser Ser Xaa Gln Ser Gly
 1               5

<210> SEQ ID NO 64
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (3)...(3)
<223> OTHER INFORMATION: cyclohexylglycine

<400> SEQUENCE: 64

Ser Ser Xaa Gln Ser Gly
 1               5

<210> SEQ ID NO 65
<211> LENGTH: 7
<212> TYPE: PRT
<213> ORGANISM: Artificial Sequence
<220> FEATURE:
```

```
<223> OTHER INFORMATION: completely synthesized
<220> FEATURE:
<221> NAME/KEY: VARIANT
<222> LOCATION: (1)...(1)
<223> OTHER INFORMATION: 3-pyridylalanine
<220> FEATURE:
<221> NAME/KEY: MOD_RES
<222> LOCATION: (7)...(7)
<223> OTHER INFORMATION: 4Hyp

<400> SEQUENCE: 65

Xaa Ser Ser Tyr Gln Ser Pro
 1               5

<210> SEQ ID NO 66
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: 3-pyridylalanine
<220> FEATURE:
<221> NAME/KEY: VARIANT
<222> LOCATION: (4)...(4)
<223> OTHER INFORMATION: cyclohexylglycine

<400> SEQUENCE: 66

Xaa Ser Ser Xaa Gln Ser Pro
 1               5

<210> SEQ ID NO 67
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: 3,4-dihydroxyproline

<400> SEQUENCE: 67

Xaa Ser Ser Tyr Gln Ser Ser Pro
 1               5

<210> SEQ ID NO 68
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: 3,4-dihydroxyproline
<220> FEATURE:
<221> NAME/KEY: MOD_RES
<222> LOCATION: (8)...(8)
<223> OTHER INFORMATION: 4Hyp

<400> SEQUENCE: 68

Xaa Ser Ser Tyr Gln Ser Ser Pro
 1               5

<210> SEQ ID NO 69
<211> LENGTH: 7
<212> TYPE: PRT
<213> ORGANISM: Artificial Sequence
```

```
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: homoarginine
<220> FEATURE:
<221> NAME/KEY: VARIANT
<222> LOCATION: (4)...(4)
<223> OTHER INFORMATION: cyclohexylglycine

<400> SEQUENCE: 69

Xaa Ser Ala Xaa Gln Ser Leu
 1               5

<210> SEQ ID NO 70
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: homoarginine
<220> FEATURE:
<221> NAME/KEY: MOD_RES
<222> LOCATION: (3)...(3)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 70

Xaa Ser Pro Xaa Gln Ser Leu
 1               5

<210> SEQ ID NO 71
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (2)...(2)
<223> OTHER INFORMATION: cyclohexylglycine

<400> SEQUENCE: 71

Pro Xaa Gln Ser Leu
 1               5

<210> SEQ ID NO 72
<211> LENGTH: 7
<212> TYPE: PRT
<213> ORGANISM: Artificial Sequence
<220> FEATURE:
<223> OTHER INFORMATION: completely synthesized

<400> SEQUENCE: 72

Asn Arg Ile Ser Tyr Gln Ser
 1               5

<210> SEQ ID NO 73
<211> LENGTH: 7
<212> TYPE: PRT
```

```
<213> ORGANISM: Artificial Sequence
<220> FEATURE:
<223> OTHER INFORMATION: completely synthesized

<400> SEQUENCE: 73

Asn Lys Val Ser Tyr Gln Ser
 1               5

<210> SEQ ID NO 74
<211> LENGTH: 10
<212> TYPE: PRT
<213> ORGANISM: Artificial Sequence
<220> FEATURE:
<223> OTHER INFORMATION: completely synthesized

<400> SEQUENCE: 74

Asn Lys Met Glu Thr Ser Tyr Gln Ser Ser
 1               5                  10

<210> SEQ ID NO 75
<211> LENGTH: 8
<212> TYPE: PRT
<213> ORGANISM: Artificial Sequence
<220> FEATURE:
<223> OTHER INFORMATION: completely synthesized

<400> SEQUENCE: 75

Asn Lys Leu Ser Tyr Gln Ser Ser
 1               5

<210> SEQ ID NO 76
<211> LENGTH: 7
<212> TYPE: PRT
<213> ORGANISM: Artificial Sequence
<220> FEATURE:
<223> OTHER INFORMATION: completely synthesized

<400> SEQUENCE: 76

Asn Lys Ile Ser Tyr Gln Ser
 1               5

<210> SEQ ID NO 77
<211> LENGTH: 8
<212> TYPE: PRT
<213> ORGANISM: Artificial Sequence
<220> FEATURE:
<223> OTHER INFORMATION: completely synthesized

<400> SEQUENCE: 77

Gln Lys Ile Ser Tyr Gln Ser Ser
 1               5

<210> SEQ ID NO 78
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (2)...(2)
<223> OTHER INFORMATION: 4Hyp

<400> SEQUENCE: 78

Asn Pro Ile Ser Tyr Gln Ser
 1               5
```

```
<210> SEQ ID NO 79
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (2)...(2)
<223> OTHER INFORMATION: 4Hyp

<400> SEQUENCE: 79

Asn Pro Val Ser Tyr Gln Ser
 1               5

<210> SEQ ID NO 80
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 4Hyp

<400> SEQUENCE: 80

Pro Ala Ser Tyr Gln Ser Ser
 1               5

<210> SEQ ID NO 81
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: 3,4-dihydroxyproline

<400> SEQUENCE: 81

Xaa Ala Ser Tyr Gln Ser Ser
 1               5

<210> SEQ ID NO 82
<211> LENGTH: 5
<212> TYPE: PRT
<213> ORGANISM: Artificial Sequence
<220> FEATURE:
<223> OTHER INFORMATION: completely synthesized
<220> FEATURE:
<221> NAME/KEY: MOD_RES
<222> LOCATION: (1)...(1)
<223> OTHER INFORMATION: 3Hyp
<220> FEATURE:
<221> NAME/KEY: VARIANT
<222> LOCATION: (3)...(3)
<223> OTHER INFORMATION: cyclohexylglycine

<400> SEQUENCE: 82

Pro Ser Xaa Gln Ser
 1               5

<210> SEQ ID NO 83
<211> LENGTH: 7
<212> TYPE: PRT
<213> ORGANISM: Artificial Sequence
<220> FEATURE:
<223> OTHER INFORMATION: completely synthesized
<220> FEATURE:
```

```
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 83

Pro Ala Ser Xaa Gln Ser Ser
 1               5

<210> SEQ ID NO 84
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 84

Xaa Ser Ser Xaa Gln Ser Ser Pro
 1               5

<210> SEQ ID NO 85
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 85

Xaa Ser Ser Xaa Gln Ser Gly
 1               5

<210> SEQ ID NO 86
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: MOD_RES
<222> LOCATION: (8)...(8)
<223> OTHER INFORMATION: MeGly

<400> SEQUENCE: 86

Xaa Ser Ser Xaa Gln Ser Ser Gly
 1               5
```

<210> SEQ ID NO 87
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 87

Xaa Ser Ser Xaa Gln Ser Ser Pro
 1               5

<210> SEQ ID NO 88
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 88

Xaa Ser Ser Xaa Gln Ser Val
 1               5

<210> SEQ ID NO 89
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (8)...(8)
<223> OTHER INFORMATION: 4-trans-L-hydroxyproline

<400> SEQUENCE: 89

Xaa Ser Ser Xaa Gln Ser Ser Xaa
 1               5

<210> SEQ ID NO 90
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl-2-aminobutyric acid

```
<220> FEATURE:
<221> NAME/KEY: VARIANT
<222> LOCATION: (4)...(4)
<223> OTHER INFORMATION: cyclohexylglycine

<400> SEQUENCE: 90

Xaa Ser Ser Xaa Gln Ser Pro
 1               5

<210> SEQ ID NO 91
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-hydroxyacetyl-2-aminobutyric acid
<220> FEATURE:
<221> NAME/KEY: VARIANT
<222> LOCATION: (4)...(4)
<223> OTHER INFORMATION: cyclohexylglycine

<400> SEQUENCE: 91

Xaa Ser Ser Xaa Gln Ser Pro
 1               5

<210> SEQ ID NO 92
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-3-pyridylalanine
<220> FEATURE:
<221> NAME/KEY: VARIANT
<222> LOCATION: (4)...(4)
<223> OTHER INFORMATION: cyclohexylglycine

<400> SEQUENCE: 92

Xaa Ser Ser Xaa Gln Ser Ser Pro
 1               5

<210> SEQ ID NO 93
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 93

Xaa Ser Ser Xaa Gln Ser Val
 1               5

<210> SEQ ID NO 94
<211> LENGTH: 7
<212> TYPE: PRT
<213> ORGANISM: Artificial Sequence
<220> FEATURE:
```

```
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 94

Xaa Ser Ser Xaa Gln Ser Leu
 1               5

<210> SEQ ID NO 95
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclcohexylglycine
<220> FEATURE:
<221> NAME/KEY: VARIANT
<222> LOCATION: (8)...(8)
<223> OTHER INFORMATION: 4-trans-L-hydroxyproline

<400> SEQUENCE: 95

Xaa Ser Ser Xaa Gln Ser Ser Xaa
 1               5

<210> SEQ ID NO 96
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 96

Xaa Ser Ser Xaa Gln Ser Pro
 1               5

<210> SEQ ID NO 97
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-3-pyridylalanine
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (6)...(6)
```

<223> OTHER INFORMATION: d-serine

<400> SEQUENCE: 97

Xaa Ser Ser Xaa Gln Xaa Pro
 1               5

<210> SEQ ID NO 98
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-methyl serine
<220> FEATURE:
<221> NAME/KEY: VARIANT
<222> LOCATION: (3)...(3)
<223> OTHER INFORMATION: cyclohexylglycine

<400> SEQUENCE: 98

Xaa Ser Xaa Gln Ser Gly
 1               5

<210> SEQ ID NO 99
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl serine
<220> FEATURE:
<221> NAME/KEY: VARIANT
<222> LOCATION: (3)...(3)
<223> OTHER INFORMATION: cyclohexylglycine
<220> FEATURE:
<221> NAME/KEY: VARIANT
<222> LOCATION: (7)...(7)
<223> OTHER INFORMATION: 4-trans-L-hydroxyproline

<400> SEQUENCE: 99

Xaa Ser Xaa Gln Ser Ser Xaa
 1               5

<210> SEQ ID NO 100
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl serine
<220> FEATURE:
<221> NAME/KEY: VARIANT
<222> LOCATION: (3)...(3)
<223> OTHER INFORMATION: cyclohexylglycine

<400> SEQUENCE: 100

Xaa Ser Xaa Gln Ser Ser Pro
 1               5

<210> SEQ ID NO 101
<211> LENGTH: 8
<212> TYPE: PRT
<213> ORGANISM: Artificial Sequence

```
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (7)...(7)
<223> OTHER INFORMATION: d-serine
<220> FEATURE:
<221> NAME/KEY: VARIANT
<222> LOCATION: (8)...(8)
<223> OTHER INFORMATION: 4-trans-L-hydroxyproline

<400> SEQUENCE: 101

Xaa Ser Ser Xaa Gln Ser Xaa Xaa
 1               5

<210> SEQ ID NO 102
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 102

Xaa Ser Ser Xaa Gln Ser Leu
 1               5

<210> SEQ ID NO 103
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 103

Xaa Ser Ser Xaa Gln Ser Ala
 1               5

<210> SEQ ID NO 104
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
```

```
<222> LOCATION: (4)...(4)
<223> OTHER INFORMATION: cyclohexylglycine
<220> FEATURE:
<221> NAME/KEY: VARIANT
<222> LOCATION: (7)...(7)
<223> OTHER INFORMATION: cyclohexylglycine

<400> SEQUENCE: 104

Xaa Ser Ser Xaa Gln Ser Xaa
 1               5

<210> SEQ ID NO 105
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: MOD_RES
<222> LOCATION: (8)...(8)
<223> OTHER INFORMATION: MeGly

<400> SEQUENCE: 105

Xaa Ser Ser Xaa Gln Ser Ser Gly
 1               5

<210> SEQ ID NO 106
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl serine
<220> FEATURE:
<221> NAME/KEY: VARIANT
<222> LOCATION: (3)...(3)
<223> OTHER INFORMATION: cyclohexylglycine
<220> FEATURE:
<221> NAME/KEY: VARIANT
<222> LOCATION: (8)...(8)
<223> OTHER INFORMATION: 4-trans-L-hydroxyproline

<400> SEQUENCE: 106

Xaa Ser Xaa Gln Ser Ser Xaa
 1               5

<210> SEQ ID NO 107
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine

<400> SEQUENCE: 107
```

Xaa Ser Ser Xaa Gln Ser Ser Pro
1               5

<210> SEQ ID NO 108
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-aminobutyric acid
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (7)...(7)
<223> OTHER INFORMATION: d-serine

<400> SEQUENCE: 108

Xaa Ser Ser Xaa Gln Ser Xaa Pro
1               5

<210> SEQ ID NO 109
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-2-aminobutyric acid
<220> FEATURE:
<221> NAME/KEY: VARIANT
<222> LOCATION: (4)...(4)
<223> OTHER INFORMATION: cyclohexylglycine

<400> SEQUENCE: 109

Xaa Ser Ser Xaa Gln Ser Ser Pro
1               5

<210> SEQ ID NO 110
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-2-aminobutyric acid
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (6)...(6)
<223> OTHER INFORMATION: d-serine

<400> SEQUENCE: 110

Xaa Ser Ser Xaa Gln Xaa Pro
1               5

<210> SEQ ID NO 111
<211> LENGTH: 7
<212> TYPE: PRT

```
<213> ORGANISM: Artificial Sequence
<220> FEATURE:
<223> OTHER INFORMATION: completely synthesized
<220> FEATURE:
<221> NAME/KEY: ACETYLATION
<222> LOCATION: (1)...(1)
<223> OTHER INFORMATION: N-acetyl serine
<220> FEATURE:
<221> NAME/KEY: VARIANT
<222> LOCATION: (3)...(3)
<223> OTHER INFORMATION: cyclohexylglycine

<400> SEQUENCE: 111

Xaa Ser Xaa Gln Ser Ser Pro
 1               5

<210> SEQ ID NO 112
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (3)...(3)
<223> OTHER INFORMATION: cyclohexylglycine
<220> FEATURE:
<221> NAME/KEY: CONFLICT
<222> LOCATION: (6)...(6)
<223> OTHER INFORMATION: d-serine
<220> FEATURE:
<221> NAME/KEY: VARIANT
<222> LOCATION: (7)...(7)
<223> OTHER INFORMATION: 4-trans-L-hydroxyproline

<400> SEQUENCE: 112

Xaa Ser Xaa Gln Ser Xaa Pro
 1               5

<210> SEQ ID NO 113
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (6)...(6)
<223> OTHER INFORMATION: d-serine

<400> SEQUENCE: 113

Xaa Ser Ser Xaa Gln Xaa Ser Pro
 1               5

<210> SEQ ID NO 114
<211> LENGTH: 8
<212> TYPE: PRT
<213> ORGANISM: Artificial Sequence
<220> FEATURE:
<223> OTHER INFORMATION: completely synthesized
<220> FEATURE:
```

```
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (5)...(5)
<223> OTHER INFORMATION: d-glutamine

<400> SEQUENCE: 114

Xaa Ser Ser Xaa Xaa Ser Ser Pro
 1               5

<210> SEQ ID NO 115
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (5)...(5)
<223> OTHER INFORMATION: d-glutamine
<220> FEATURE:
<221> NAME/KEY: VARIANT
<222> LOCATION: (6)...(6)
<223> OTHER INFORMATION: d-serine

<400> SEQUENCE: 115

Xaa Ser Ser Xaa Xaa Xaa Ser Pro
 1               5

<210> SEQ ID NO 116
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine

<400> SEQUENCE: 116

Xaa Xaa Gln Ser Ser Pro
 1               5

<210> SEQ ID NO 117
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
```

```
<221> NAME/KEY: VARIANT
<222> LOCATION: (2)...(2)
<223> OTHER INFORMATION: cyclohexylglycine
<220> FEATURE:
<221> NAME/KEY: VARIANT
<222> LOCATION: (6)...(6)
<223> OTHER INFORMATION: 4-trans-L-hydroxyproline

<400> SEQUENCE: 117

Xaa Xaa Gln Ser Ser Xaa
 1               5

<210> SEQ ID NO 118
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine
<220> FEATURE:
<221> NAME/KEY: MOD_RES
<222> LOCATION: (6)...(6)
<223> OTHER INFORMATION: MeGly

<400> SEQUENCE: 118

Xaa Xaa Gln Ser Ser Gly
 1               5

<210> SEQ ID NO 119
<211> LENGTH: 7
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine
<220> FEATURE:
<221> NAME/KEY: MOD_RES
<222> LOCATION: (6)...(6)
<223> OTHER INFORMATION: Aib

<400> SEQUENCE: 119

Xaa Xaa Gln Ser Ser Ala Pro
 1               5

<210> SEQ ID NO 120
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine
<220> FEATURE:
```

```
<221> NAME/KEY: VARIANT
<222> LOCATION: (6)...(6)
<223> OTHER INFORMATION: N-methyl-alanine

<400> SEQUENCE: 120

Xaa Xaa Gln Ser Ser Xaa
 1               5

<210> SEQ ID NO 121
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine
<220> FEATURE:
<221> NAME/KEY: MOD_RES
<222> LOCATION: (5)...(5)
<223> OTHER INFORMATION: Aib

<400> SEQUENCE: 121

Xaa Xaa Gln Ser Ala Pro
 1               5

<210> SEQ ID NO 122
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-hydroxyacetyl serine
<220> FEATURE:
<221> NAME/KEY: VARIANT
<222> LOCATION: (2)...(2)
<223> OTHER INFORMATION: cyclohexylglycine
<220> FEATURE:
<221> NAME/KEY: MOD_RES
<222> LOCATION: (6)...(6)
<223> OTHER INFORMATION: MeGly

<400> SEQUENCE: 122

Xaa Xaa Gln Ser Ser Gly
 1               5

<210> SEQ ID NO 123
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
```

```
<223> OTHER INFORMATION: cyclohexylglycine
<220> FEATURE:
<221> NAME/KEY: VARIANT
<222> LOCATION: (6)...(6)
<223> OTHER INFORMATION: pipecolinic acid

<400> SEQUENCE: 123

Xaa Xaa Gln Ser Ser Xaa
 1               5

<210> SEQ ID NO 124
<211> LENGTH: 8
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl-4-trans-L-hydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (8)...(8)
<223> OTHER INFORMATION: pipecolinic acid

<400> SEQUENCE: 124

Xaa Ser Ser Xaa Gln Ser Ser Xaa
 1               5

<210> SEQ ID NO 125
<211> LENGTH: 6
<212> TYPE: PRT
<213> ORGANISM: Artificial Sequence
<220> FEATURE:
<223> OTHER INFORMATION: completely synthesized
<220> FEATURE:
<221> NAME/KEY: VARIANT
<222> LOCATION: (1)...(1)
<223> OTHER INFORMATION: N-acetyl serine
<220> FEATURE:
<221> NAME/KEY: VARIANT
<222> LOCATION: (2)...(2)
<223> OTHER INFORMATION: cyclohexylglycine
<220> FEATURE:
<221> NAME/KEY: VARIANT
<222> LOCATION: (6)...(6)
<223> OTHER INFORMATION: N-methyl-d-alanine

<400> SEQUENCE: 125

Xaa Xaa Gln Ser Ser Xaa
 1               5
```